US008795327B2

(12) United States Patent
Dietz et al.

(10) Patent No.: US 8,795,327 B2
(45) Date of Patent: Aug. 5, 2014

(54) ELECTROSURGICAL INSTRUMENT WITH SEPARATE CLOSURE AND CUTTING MEMBERS

(75) Inventors: Timothy G. Dietz, Terrace Park, OH (US); Mary E. Mootoo, Cincinnati, OH (US); David A. Witt, Maineville, OH (US); Zhifan F. Huang, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1024 days.

(21) Appl. No.: 12/841,480

(22) Filed: Jul. 22, 2010

(65) Prior Publication Data
US 2012/0022525 A1 Jan. 26, 2012

(51) Int. Cl.
*A61B 18/14* (2006.01)
*A61B 18/08* (2006.01)
*A61B 18/00* (2006.01)

(52) U.S. Cl.
CPC .......... *A61B 18/1445* (2013.01); *A61B 18/085* (2013.01); *A61B 2018/1455* (2013.01); *A61B 2018/00607* (2013.01)
USPC .................. 606/207; 607/51; 607/52; 607/37

(58) Field of Classification Search
CPC ............. A61B 2018/00607; A61B 2018/1455; A61B 18/1445; A61B 18/085
USPC ............. 606/51, 52, 37, 307, 207; 227/175.1, 227/180.1
See application file for complete search history.

(56) References Cited

U.S. PATENT DOCUMENTS

| 4,005,714 A | 2/1977 | Hiltebrandt |
| 4,220,154 A | 9/1980 | Semm |
| 5,522,839 A | 6/1996 | Pilling |
| 5,665,100 A | 9/1997 | Yoon |
| 5,752,973 A | 5/1998 | Kieturakis |

(Continued)

FOREIGN PATENT DOCUMENTS

| DE | 10201569 | 7/2003 |
| EP | 0705571 A1 | 4/1996 |

(Continued)

OTHER PUBLICATIONS

U.S. Appl. No. 13/221,410, filed Aug. 30, 2011.

(Continued)

*Primary Examiner* — Linda Dvorak
*Assistant Examiner* — Jocelyn D Ram

(57) ABSTRACT

In various embodiments, a surgical instrument is provided that may comprise an end effector for performing a surgical procedure on tissue, for example. The end effector may comprise a pair of jaws, a closure beam, and a cutting member. The closure beam and the cutting member may be releasably coupled together by an interlocking member such that movement of the cutting member may cause the closure beam to also move relative to the jaws and cause the jaws to close and grip tissue, for example. The interlocking member may then unlock, allowing the cutting member to move through the gripped tissue and relative to the closure beam. Additionally, the cutting member and closure beam may be operated by a single trigger, which may be configured to provide haptic feedback to a user at various stages. Further, the jaws may be electrically energized to deliver energy and/or seal the gripped tissue.

26 Claims, 16 Drawing Sheets

(56) References Cited

U.S. PATENT DOCUMENTS

| | | | |
|---|---|---|---|
| 5,984,938 A | 11/1999 | Yoon | |
| 6,013,052 A | 1/2000 | Durman et al. | |
| 6,068,629 A | 5/2000 | Haissaguerre et al. | |
| 6,206,876 B1 | 3/2001 | Levine et al. | |
| 6,443,968 B1 | 9/2002 | Holthaus et al. | |
| 6,458,128 B1* | 10/2002 | Schulze | 606/50 |
| 6,464,702 B2* | 10/2002 | Schulze et al. | 606/51 |
| 6,500,176 B1* | 12/2002 | Truckai et al. | 606/51 |
| 6,514,252 B2 | 2/2003 | Nezhat et al. | |
| 6,554,829 B2* | 4/2003 | Schulze et al. | 606/51 |
| 6,572,639 B1 | 6/2003 | Ingle et al. | |
| 6,623,482 B2* | 9/2003 | Pendekanti et al. | 606/51 |
| 6,635,057 B2 | 10/2003 | Harano et al. | |
| 6,656,177 B2* | 12/2003 | Truckai et al. | 606/51 |
| 6,679,882 B1 | 1/2004 | Kornerup | |
| 6,695,840 B2* | 2/2004 | Schulze | 606/50 |
| 6,770,072 B1* | 8/2004 | Truckai et al. | 606/52 |
| 6,773,435 B2* | 8/2004 | Schulze et al. | 606/51 |
| 6,800,085 B2 | 10/2004 | Selmon et al. | |
| 6,860,880 B2 | 3/2005 | Treat et al. | |
| 6,905,497 B2* | 6/2005 | Truckai et al. | 606/49 |
| 6,926,716 B2* | 8/2005 | Baker et al. | 606/51 |
| 6,929,644 B2* | 8/2005 | Truckai et al. | 606/51 |
| 6,953,461 B2 | 10/2005 | McClurken et al. | |
| 7,011,657 B2* | 3/2006 | Truckai et al. | 606/51 |
| 7,063,699 B2* | 6/2006 | Hess et al. | 606/51 |
| 7,066,936 B2 | 6/2006 | Ryan | |
| 7,087,054 B2* | 8/2006 | Truckai et al. | 606/51 |
| 7,101,372 B2 | 9/2006 | Dycus et al. | |
| 7,112,201 B2* | 9/2006 | Truckai et al. | 606/51 |
| 7,189,233 B2* | 3/2007 | Truckai et al. | 606/51 |
| 7,207,471 B2 | 4/2007 | Heinrich et al. | |
| 7,220,951 B2 | 5/2007 | Truckai et al. | |
| 7,311,709 B2* | 12/2007 | Truckai et al. | 606/51 |
| 7,329,257 B2 | 2/2008 | Kanehira et al. | |
| 7,381,209 B2* | 6/2008 | Truckai et al. | 606/51 |
| 7,597,693 B2 | 10/2009 | Garrison | |
| 7,604,150 B2 | 10/2009 | Boudreaux | |
| 7,628,792 B2 | 12/2009 | Guerra | |
| 7,658,311 B2 | 2/2010 | Boudreaux | |
| 7,666,206 B2 | 2/2010 | Taniguchi et al. | |
| 7,815,641 B2 | 10/2010 | Dodde et al. | |
| 7,879,035 B2 | 2/2011 | Garrison et al. | |
| 7,931,649 B2 | 4/2011 | Couture et al. | |
| 7,935,114 B2 | 5/2011 | Takashino et al. | |
| 8,460,292 B2* | 6/2013 | Truckai et al. | 606/51 |
| 8,496,682 B2* | 7/2013 | Guerra et al. | 606/205 |
| 8,535,311 B2* | 9/2013 | Schall | 606/51 |
| 2002/0099371 A1* | 7/2002 | Schulze et al. | 606/51 |
| 2002/0099372 A1* | 7/2002 | Schulze et al. | 606/51 |
| 2002/0099373 A1* | 7/2002 | Schulze et al. | 606/51 |
| 2002/0099374 A1* | 7/2002 | Pendekanti et al. | 606/51 |
| 2002/0099375 A1* | 7/2002 | Hess et al. | 606/51 |
| 2002/0115997 A1* | 8/2002 | Truckai et al. | 606/51 |
| 2002/0198525 A1* | 12/2002 | Schulze et al. | 606/51 |
| 2003/0078577 A1* | 4/2003 | Truckai et al. | 606/51 |
| 2003/0114851 A1* | 6/2003 | Truckai et al. | 606/51 |
| 2003/0158548 A1 | 8/2003 | Phan et al. | |
| 2003/0199870 A1* | 10/2003 | Truckai et al. | 606/51 |
| 2004/0193150 A1 | 9/2004 | Sharkey et al. | |
| 2004/0199161 A1* | 10/2004 | Truckai et al. | 606/48 |
| 2005/0085809 A1 | 4/2005 | Mucko et al. | |
| 2005/0096651 A1* | 5/2005 | Truckai et al. | 606/51 |
| 2005/0159745 A1* | 7/2005 | Truckai et al. | 606/51 |
| 2005/0165429 A1 | 7/2005 | Douglas et al. | |
| 2005/0171535 A1* | 8/2005 | Truckai et al. | 606/48 |
| 2005/0203507 A1* | 9/2005 | Truckai et al. | 606/51 |
| 2006/0069388 A1* | 3/2006 | Truckai et al. | 606/45 |
| 2006/0217709 A1 | 9/2006 | Couture et al. | |
| 2006/0293656 A1* | 12/2006 | Shadduck et al. | 606/51 |
| 2007/0129728 A1* | 6/2007 | Truckai et al. | 606/51 |
| 2007/0260242 A1* | 11/2007 | Dycus et al. | |
| 2008/0147062 A1* | 6/2008 | Truckai et al. | 606/51 |
| 2008/0188851 A1* | 8/2008 | Truckai et al. | 606/52 |
| 2008/0221565 A1 | 9/2008 | Eder et al. | |
| 2008/0294158 A1 | 11/2008 | Pappone et al. | |
| 2009/0076506 A1* | 3/2009 | Baker | 606/51 |
| 2009/0125027 A1 | 5/2009 | Fischer | |
| 2009/0320268 A1 | 12/2009 | Cunningham et al. | |
| 2010/0036370 A1* | 2/2010 | Mirel et al. | 606/33 |
| 2010/0036380 A1 | 2/2010 | Taylor et al. | |
| 2010/0274244 A1* | 10/2010 | Heard | 606/45 |
| 2011/0087208 A1 | 4/2011 | Boudreaux et al. | |
| 2011/0087209 A1 | 4/2011 | Boudreaux et al. | |
| 2011/0087218 A1 | 4/2011 | Boudreaux et al. | |
| 2011/0087219 A1 | 4/2011 | Boudreaux et al. | |
| 2011/0087220 A1 | 4/2011 | Felder et al. | |
| 2011/0238065 A1* | 9/2011 | Hunt et al. | 606/45 |
| 2011/0251608 A1 | 10/2011 | Timm et al. | |
| 2011/0251609 A1* | 10/2011 | Johnson et al. | 606/46 |
| 2011/0251612 A1* | 10/2011 | Faller et al. | 606/52 |
| 2011/0251613 A1* | 10/2011 | Guerra et al. | 606/52 |
| 2011/0264093 A1* | 10/2011 | Schall | 606/52 |
| 2011/0282339 A1* | 11/2011 | Weizman et al. | 606/33 |
| 2011/0306963 A1* | 12/2011 | Dietz et al. | 606/41 |
| 2011/0306964 A1* | 12/2011 | Stulen et al. | 606/41 |
| 2011/0306965 A1* | 12/2011 | Norvell et al. | 606/41 |
| 2011/0306966 A1* | 12/2011 | Dietz et al. | 606/41 |
| 2011/0306967 A1 | 12/2011 | Payne et al. | |
| 2011/0306968 A1* | 12/2011 | Beckman et al. | 606/41 |
| 2011/0306972 A1* | 12/2011 | Widenhouse et al. | 606/45 |
| 2011/0306973 A1* | 12/2011 | Cummings et al. | 606/48 |
| 2012/0010616 A1* | 1/2012 | Huang et al. | 606/52 |
| 2012/0022525 A1* | 1/2012 | Dietz et al. | 606/45 |
| 2012/0150176 A1* | 6/2012 | Weizman | 606/45 |
| 2013/0030433 A1* | 1/2013 | Heard | 606/45 |
| 2013/0079762 A1* | 3/2013 | Twomey et al. | 606/29 |

FOREIGN PATENT DOCUMENTS

| | | |
|---|---|---|
| EP | 0640317 B1 | 9/1999 |
| EP | 1849424 B1 | 4/2009 |
| EP | 2060238 A1 | 5/2009 |
| EP | 1810625 B1 | 8/2009 |
| EP | 2090238 A1 | 8/2009 |
| EP | 2092905 A1 | 8/2009 |
| EP | 1747761 B1 | 10/2009 |
| EP | 1769766 B1 | 2/2010 |
| EP | 2151204 A1 | 2/2010 |
| EP | 2243439 A1 | 10/2010 |
| WO | WO 93/22973 A1 | 11/1993 |
| WO | WO 96/35382 A1 | 11/1996 |
| WO | WO 98/57588 A1 | 12/1998 |
| WO | WO 99/40861 A1 | 8/1999 |
| WO | WO 00/25691 A1 | 5/2000 |
| WO | WO 03/013374 A1 | 2/2003 |
| WO | WO 03/020339 A2 | 3/2003 |
| WO | WO 03/028541 A2 | 4/2003 |
| WO | WO 03/068046 A2 | 8/2003 |
| WO | WO 2006/021269 A1 | 3/2006 |
| WO | WO 2006/036706 A1 | 4/2006 |
| WO | WO 2006/055166 A2 | 5/2006 |
| WO | WO 2008/045348 A2 | 4/2008 |
| WO | WO 2008/099529 A1 | 8/2008 |
| WO | WO 2009/022614 A1 | 2/2009 |
| WO | WO 2009/059741 A1 | 5/2009 |
| WO | WO 2009/082477 A2 | 7/2009 |
| WO | WO 2010/104755 A1 | 9/2010 |
| WO | WO 2011/089717 A1 | 7/2011 |

OTHER PUBLICATIONS

U.S. Appl. No. 13/189,169, filed Jul. 22, 2011.

\* cited by examiner

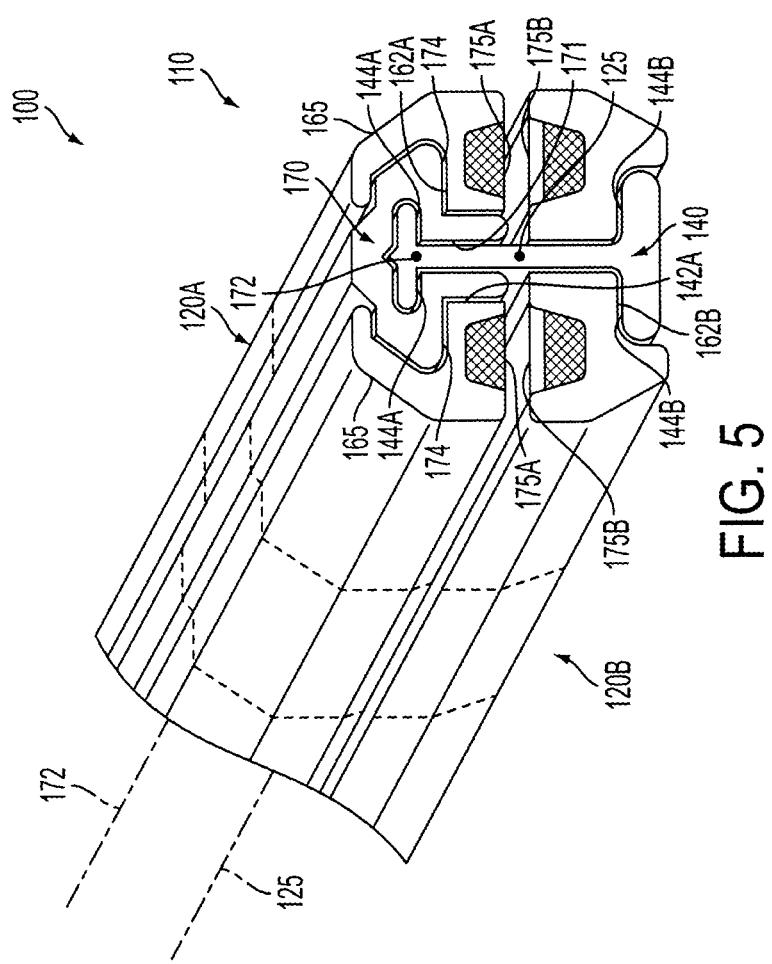

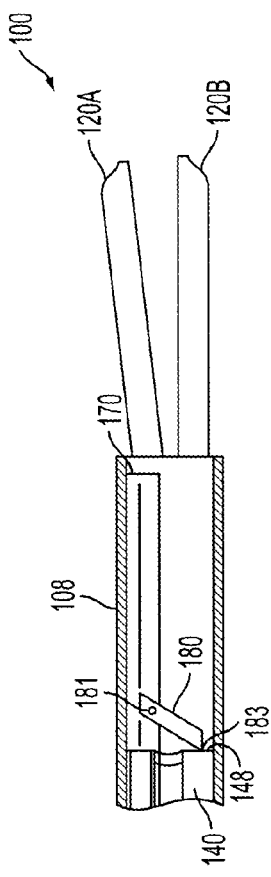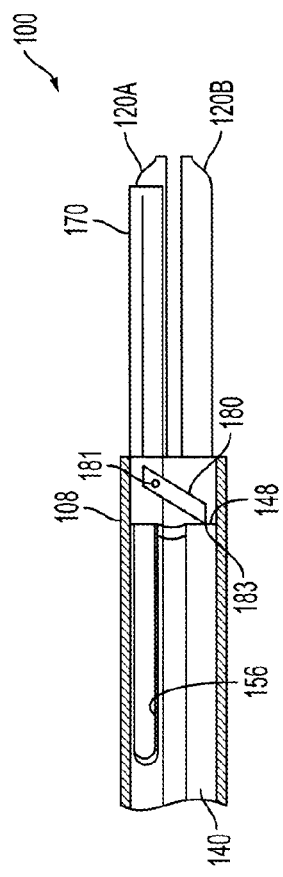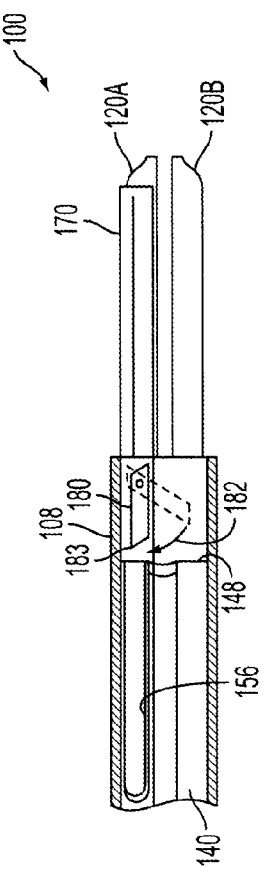

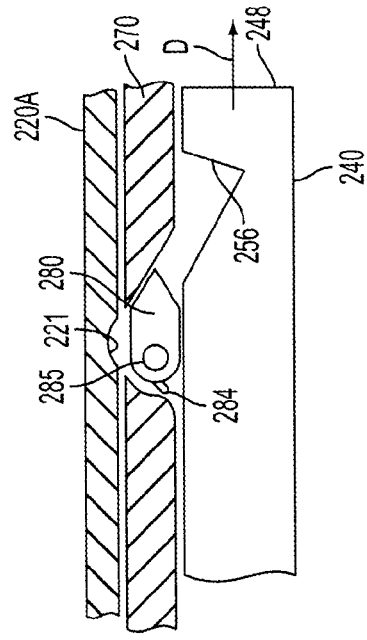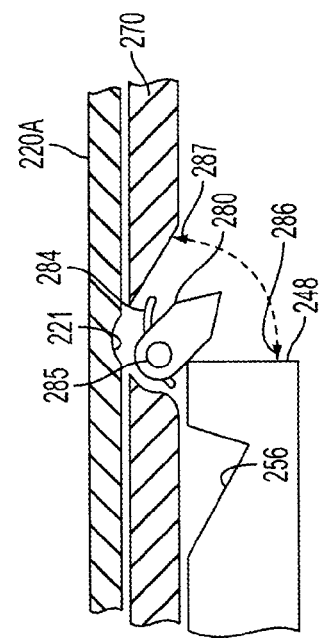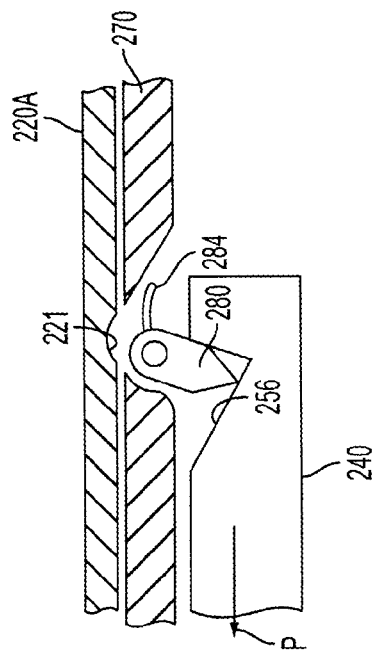

ELECTROSURGICAL INSTRUMENT WITH SEPARATE CLOSURE AND CUTTING MEMBERS

BACKGROUND

The present disclosure is directed to medical devices and methods, and, more particularly, to electrosurgical instruments and methods for sealing and transecting tissue.

In various circumstances, a surgical instrument can be configured to apply energy to tissue in order to treat and/or destroy the tissue. In certain circumstances, a surgical instrument can comprise one or more electrodes which can be positioned against and/or positioned relative to the tissue such that electrical current can flow from one electrode, through the tissue, and to the other electrode. The surgical instrument can comprise an electrical input, a supply conductor electrically coupled with the electrodes, and/or a return conductor which can be configured to allow current to flow from the electrical input, through the supply conductor, through the electrodes and the tissue, and then through the return conductor to an electrical output, for example. In various circumstances, heat can be generated by the current flowing through the tissue, wherein the heat can cause one or more hemostatic seals to form within the tissue and/or between tissues. Such embodiments may be particularly useful for sealing blood vessels, for example. The surgical instrument can also comprise a cutting member that can be moved relative to the tissue and the electrodes in order to transect the tissue.

By way of example, energy applied by a surgical instrument may be in the form of radio frequency ("RF") energy. RF energy is a form of electrical energy that may be in the frequency range of 300 kilohertz (kHz) to 1 megahertz (MHz). In application, RF surgical instruments transmit low frequency radio waves through electrodes, which cause ionic agitation, or friction, increasing the temperature of the tissue. Since a sharp boundary is created between the affected tissue and that surrounding it, surgeons can operate with a high level of precision and control, without much sacrifice to the adjacent normal tissue. The low operating temperatures of RF energy enables surgeons to remove, shrink or sculpt soft tissue while simultaneously sealing blood vessels. RF energy works particularly well on connective tissue, which is primarily comprised of collagen and shrinks when contacted by heat.

Further, in various open and laparoscopic surgeries, it may be necessary to coagulate, seal or fuse tissues. One means of sealing tissue relies upon the application of electrical energy to tissue captured within an end effector of a surgical instrument in order to cause thermal effects within the tissue. Various mono-polar and bi-polar RF jaw structures have been developed for such purposes. In general, the delivery of RF energy to the captured tissue elevates the temperature of the tissue and, as a result, the energy can at least partially denature proteins within the tissue. Such proteins, such as collagen, for example, may be denatured into a proteinaceous amalgam that intermixes and fuses, or "welds," together as the proteins renature. As the treated region heals over time, this biological "weld" may be reabsorbed by the body's wound healing process.

In certain arrangements of a bi-polar radiofrequency (RF) jaw, the surgical instrument can comprise opposing first and second jaws, wherein the face of each jaw can comprise an electrode. In use, the tissue can be captured between the jaw faces such that electrical current can flow between the electrodes in the opposing jaws and through the tissue positioned therebetween. Such instruments may have to seal or "weld" many types of tissues, such as anatomic structures having walls with irregular or thick fibrous content, bundles of disparate anatomic structures, substantially thick anatomic structures, and/or tissues with thick fascia layers such as large diameter blood vessels, for example. With particular regard to sealing large diameter blood vessels, for example, such applications may require a high strength tissue weld immediately post-treatment.

The foregoing discussion is intended only to illustrate the present field and should not be taken as a disavowal of claim scope.

SUMMARY

In various embodiments, a surgical instrument is provided. In at least one embodiment, the surgical instrument can comprise an end effector comprising a first jaw defining a channel, a second jaw, a closure beam, and a cutting member. In these embodiments, the first jaw and the second jaw can be operably coupled together such that the first jaw may move between an open position and a closed position with respect to the second jaw. Additionally, in these embodiments, the closure beam can be sized and configured to fit at least partially within the channel and the closure beam can be configured to translate along the channel between a first position and a second position. Further, in these embodiments, the first jaw may be at the closed position when the closure beam is at the second position. Also, in these embodiments, the cutting member can be sized and configured to fit at least partially within the channel. Moreover, the cutting member can be configured to translate along the channel and with respect to the closure beam.

In at least one embodiment, a surgical instrument is provided that can comprise an end effector comprising a first jaw including a tissue contacting surface, a second jaw, a closure beam operably contacting the first jaw, and a cutting member defining a longitudinal axis. In these embodiments, the first jaw and the second jaw can be operably coupled together such that the first jaw may move between an open position and a closed position with respect to the second jaw. Additionally, in these embodiments, the closure beam can be configured to translate with respect to the first jaw between a first position and a second position. Further, in these embodiments, the first jaw can be urged to the closed position by the closure beam when the closure beam is at the second position. Also, in these embodiments, the cutting member can be configured to translate with respect to the first jaw between a retracted position and a fully advanced position. Additionally, in these embodiments, the cutting member can be configured to translate with respect to the closure beam. Moreover, in these embodiments, a plane perpendicular to the cutting member's longitudinal axis can transect the first jaw's tissue contacting surface, the closure beam, and the cutting member when the closure beam is at the second position and the cutting member is at the fully advanced position.

In at least one embodiment, a surgical instrument is provided that can comprise an end effector comprising a first jaw, a second jaw, a closure beam operably contacting the first jaw, a cutting member configured to translate with respect to the first jaw, and an interlocking member. In these embodiments, the first jaw and the second jaw can be operably coupled together such that the first jaw may move between an open position and a closed position with respect to the second jaw. Additionally, in these embodiments, the closure beam can be configured to translate with respect to the first jaw between a first position and a second position. Also, in these embodiments, the first jaw can be urged to the closed position by the closure beam when the closure beam is at the second position. Further, in these embodiments, the cutting member can be configured to translate with respect to the closure beam. Moreover, in these embodiments, the interlocking member can be configured to selectively hold the cutting member and the closure beam together such that the cutting member and the closure beam translate synchronously with each other in at least one direction with respect to the first jaw.

The foregoing discussion should not be taken as a disavowal of claim scope.

FIGURES

Various features of the embodiments described herein are set forth with particularity in the appended claims. The various embodiments, however, both as to organization and methods of operation, together with advantages thereof, may be understood in accordance with the following description taken in conjunction with the accompanying drawings as follows.

FIG. 5 is a perspective sectional view of a portion of an end effector of the surgical instrument of FIG. 1.

FIG. 7 is a schematic side view of a distal portion of the surgical instrument of FIG. 1 showing the closure beam being advanced by the cutting member towards an open pair of jaws.

FIG. 8 is a schematic side view of a distal portion of the surgical instrument of FIG. 1 showing the closure beam fully advanced into one of the now-closed jaws.

FIG. 9 is a schematic side view of a distal portion of the surgical instrument of FIG. 6 showing the cutting member retracted distally to release a spring-loaded pawl that is rotatably mounted to the closure beam.

FIGS. 11-13 are side views of portions of a jaw, a closure beam, a pawl, and a cutting member of the surgical instrument of FIG. 10 in various configurations.

Figure 1:
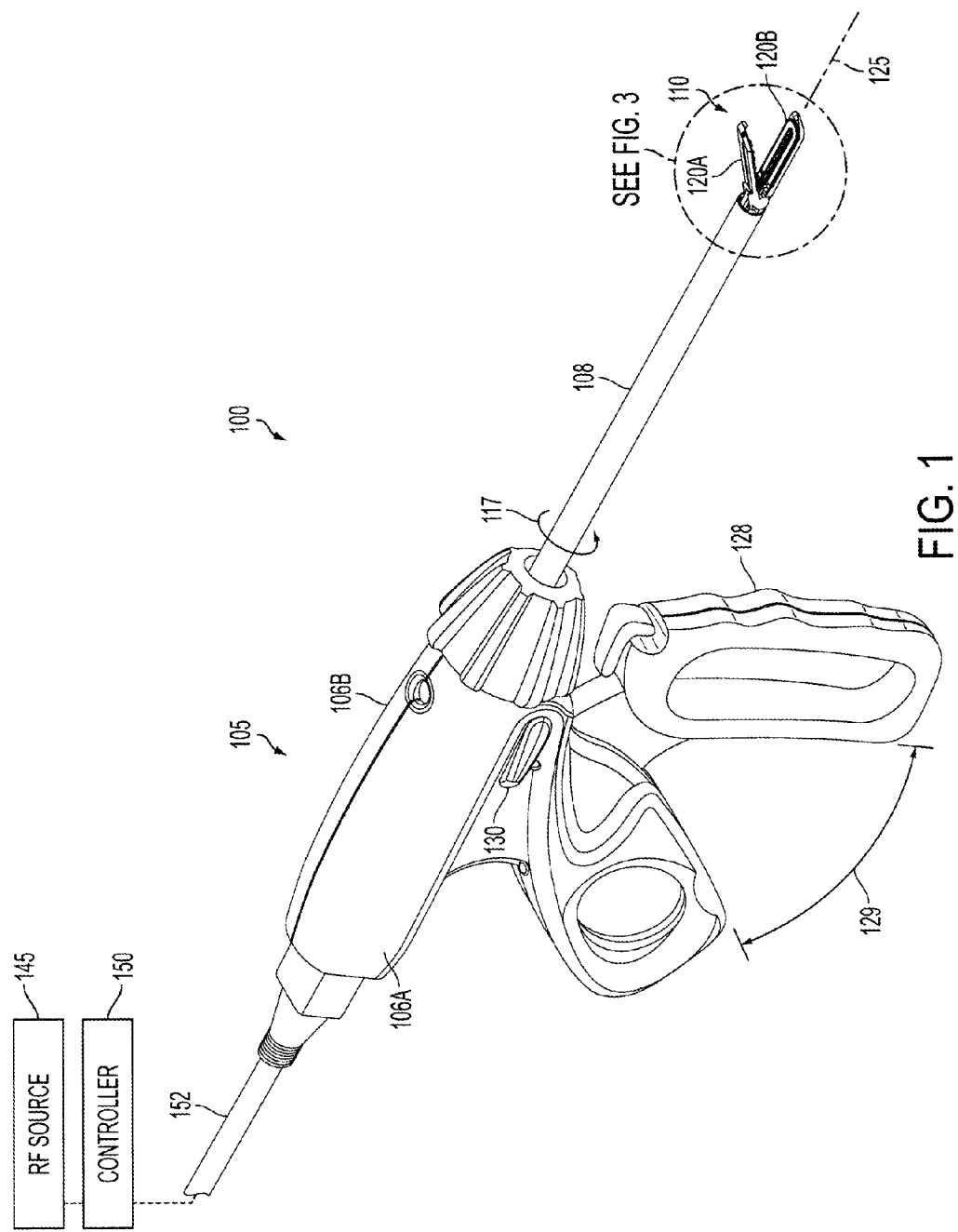
FIG. 1 is a perspective view of a surgical instrument according to a non-limiting embodiment.

Corresponding reference characters indicate corresponding parts throughout the several views. The exemplifications set out herein illustrate various embodiments, in one or more forms, and such exemplifications are not to be construed as limiting the scope of the claims in any manner.

DETAILED DESCRIPTION

Various embodiments are directed to apparatuses, systems, and methods for the treatment of tissue. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements have not been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

Reference throughout the specification to "various embodiments," "some embodiments," "one embodiment," or "an embodiment", or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located farthest from the clinician. It will be further appreciated that for conciseness and clarity, spatial terms such as "vertical," "horizontal," "up," and "down" may be used herein with respect to the illustrated embodiments. However, surgical instruments may be used in many orientations and positions, and these terms are not intended to be limiting and absolute.

The entire disclosures of the following non-provisional United States patents are hereby incorporated by reference herein:

U.S. Pat. No. 7,381,209, entitled ELECTROSURGICAL INSTRUMENT;

U.S. Pat. No. 7,354,440, entitled ELECTROSURGICAL INSTRUMENT AND METHOD OF USE;

U.S. Pat. No. 7,311,709, entitled ELECTROSURGICAL INSTRUMENT AND METHOD OF USE;

U.S. Pat. No. 7,309,849, entitled POLYMER COMPOSITIONS EXHIBITING A PTC PROPERTY AND METHODS OF FABRICATION;

U.S. Pat. No. 7,220,951, entitled SURGICAL SEALING SURFACES AND METHODS OF USE;

U.S. Pat. No. 7,189,233, entitled ELECTROSURGICAL INSTRUMENT;

U.S. Pat. No. 7,186,253, entitled ELECTROSURGICAL JAW STRUCTURE FOR CONTROLLED ENERGY DELIVERY;

U.S. Pat. No. 7,169,146, entitled ELECTROSURGICAL PROBE AND METHOD OF USE;

U.S. Pat. No. 7,125,409, entitled ELECTROSURGICAL WORKING END FOR CONTROLLED ENERGY DELIVERY; and U.S. Pat. No. 7,112,201, entitled ELECTROSURGICAL INSTRUMENT AND METHOD OF USE.

Various embodiments of systems and methods relate to creating thermal "welds" or "fusion" within native tissue volumes. The alternative terms of tissue "welding" and tissue "fusion" may be used interchangeably herein to describe thermal treatments of a targeted tissue volume that result in a substantially uniform fused-together tissue mass, for example, in welding blood vessels that exhibit substantial burst strength immediately post-treatment. The strength of such welds is particularly useful for (i) permanently sealing blood vessels in vessel transection procedures; (ii) welding organ margins in resection procedures; (iii) welding other anatomic ducts wherein permanent closure is required; and also (iv) for performing vessel anastomosis, vessel closure or other procedures that join together anatomic structures or portions thereof. The welding or fusion of tissue as disclosed herein is to be distinguished from "coagulation", "hemostasis" and other similar descriptive terms that generally relate to the collapse and occlusion of blood flow within small blood vessels or vascularized tissue. For example, any surface application of thermal energy can cause coagulation or hemostasis—but does not fall into the category of "welding" as the term is used herein. Such surface coagulation does not create a weld that provides any substantial strength in the treated tissue.

At the molecular level, the phenomena of truly "welding" tissue as disclosed herein may result from the thermally-induced denaturation of collagen and other protein molecules in a targeted tissue volume to create a transient liquid or gel-like proteinaceous amalgam. A selected energy density is provided in the targeted tissue to cause hydrothermal breakdown of intra- and intermolecular hydrogen crosslinks in collagen and other proteins. The denatured amalgam is maintained at a selected level of hydration—without desiccation—for a selected time interval which can be very brief. The targeted tissue volume is maintained under a selected very high level of mechanical compression to insure that the unwound strands of the denatured proteins are in close proximity to allow their intertwining and entanglement. Upon thermal relaxation, the intermixed amalgam results in protein entanglement as re-crosslinking or renaturation occurs to thereby cause a uniform fused-together mass.

A surgical instrument can be configured to supply energy, such as electrical energy, ultrasonic energy, and/or heat energy, for example, to the tissue of a patient. For example, various embodiments disclosed herein provide electrosurgical jaw structures adapted for transecting captured tissue between the jaws and for contemporaneously welding or sealing the captured tissue margins with controlled application of RF energy. In more detail, in various embodiments, referring now to FIG. 1, an electrosurgical instrument 100 is shown. Surgical or electrosurgical instrument 100 can comprise a proximal handle 105, a distal working end or end effector 110 and an introducer or elongate shaft 108 disposed in-between and at least partially operably coupling the handle 105 to the end effector 110. End effector 110 may comprise a set of openable-closeable jaws with straight or curved jaws—an upper first jaw 120A and a lower second jaw 120B. The jaws 120A and 120B may be operably coupled together such that the first jaw 120A may move between an open position (see FIG. 3) and a closed position (see FIG. 4) with respect to the second jaw 120B. First jaw 120A and second jaw 120B may each comprise an elongate slot or channel 142A and 142B (see FIG. 3), respectively, disposed outwardly along their respective middle portions. First jaw 120A and second jaw 120B may be coupled to an electrical source 145 and a controller 150 through electrical leads in cable 152. Controller 150 may be used to activate electrical source 145. In various embodiments, the electrical source 145 may comprise an RF source, an ultrasonic source, a direct current source, and/or any other suitable type of electrical energy source, for example.

Figure 2:
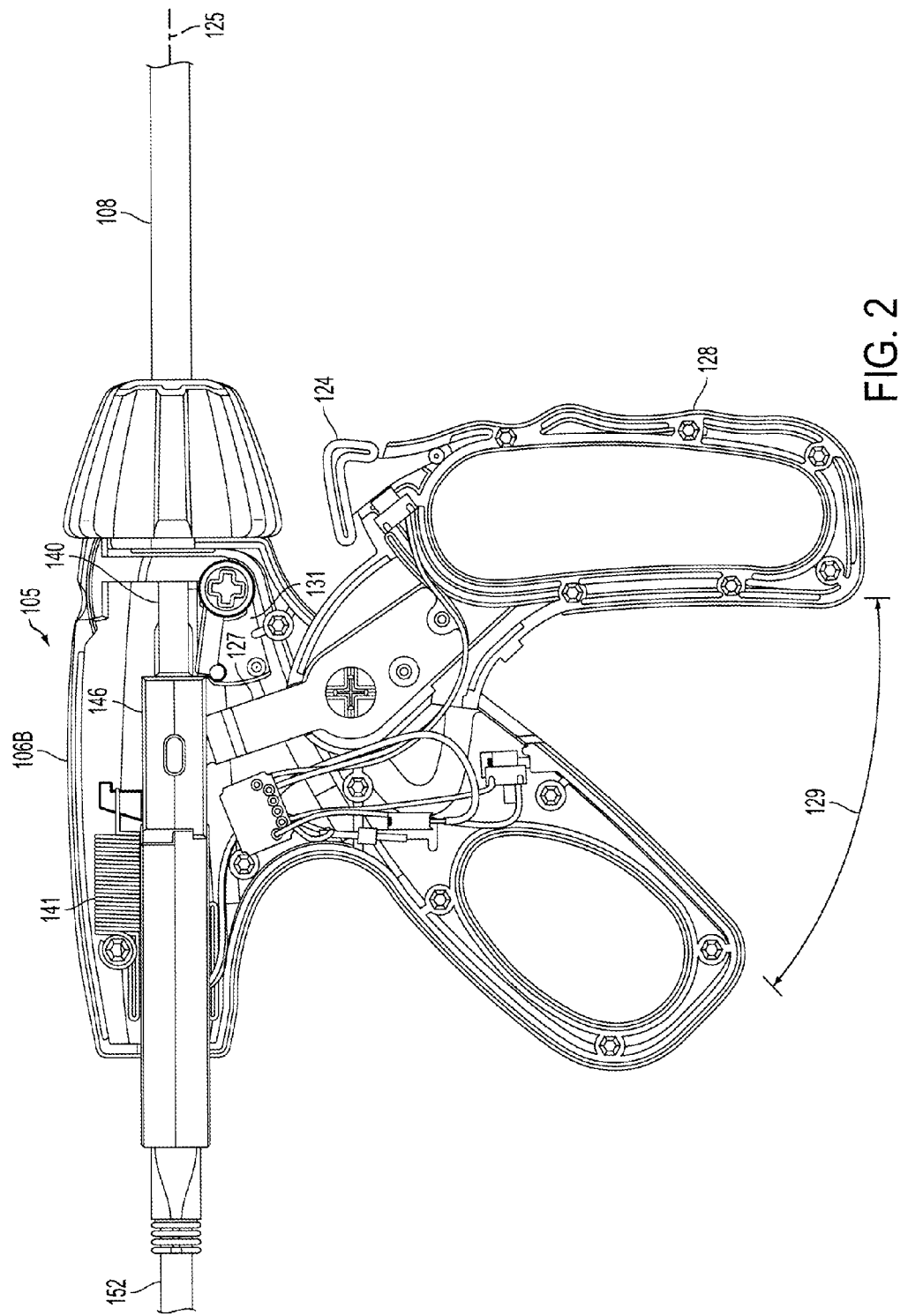
FIG. 2 is a side view of a handle of the surgical instrument of FIG. 1 with a half of a handle body removed to illustrate some of the components therein.

Moving now to FIG. 2, a side view of the handle 105 is shown with half of a first handle body 106A (see FIG. 1) removed to illustrate some of the components within second handle body 106B. Handle 105 may comprise a lever arm or trigger 128 extending from the handle body 106A and/or 106B. The trigger 128 may be pulled along a path 129 such that the trigger 128 moves with respect to body 106A and/or 106B. The trigger 128 may also be operably coupled to a movable cutting member 140 disposed within elongate shaft 108 by a shuttle 146 operably engaged to an extension 127 of trigger 128. Accordingly, movement of the trigger 128 relative to the handle body 106A and/or 106B may cause the cutting member 140 to translate with respect to one or both of jaws 120A and 120B (see FIG. 1). Also, as described in more detail below, the cutting member 140 may be releasably engaged with a closure beam 170 (see FIGS. 3-4) that is also movably associated with the jaws 120A, 120B. The shuttle 146 may further be connected to a biasing device, such as spring 141, which may also be connected to the second handle body 106B, to bias the shuttle 146 and thus the cutting member 140 and/or the closure beam 170 (FIG. 3) in a proximal direction, thereby urging the jaws 120A and 120B to an open position as seen in FIG. 1. Also, referring to FIGS. 1 and 2, a locking member 131 (see FIG. 2) may be moved by a locking switch 130 (see FIG. 1) between a locked position, where the shuttle 146 is substantially prevented from moving distally as illustrated, and an unlocked position, where the shuttle 146 may be allowed to freely move in the distal direction, toward the elongate shaft 108. The handle 105 can be any type of pistol-grip or other type of handle known in the art that is configured to carry actuator levers, triggers or sliders for actuating the first jaw 120A and second jaw 120B. Elongate shaft 108 may have a cylindrical or rectangular cross-section and can comprise a thin-wall tubular sleeve that extends from handle 105. Elongate shaft 108 may include a bore extending therethrough for carrying actuator mechanisms, such as cutting member 140 and/or closure beam 170, for example, for actuating the jaws and for carrying electrical leads for delivery of electrical energy to electrosurgical components of end effector 110.

End effector 110 may be adapted for capturing, welding or sealing, and transecting tissue. First jaw 120A and second jaw 120B may close to thereby capture or engage tissue about a longitudinal axis 125 defined by cutting member 140. First jaw 120A and second jaw 120B may also apply compression to the tissue. Elongate shaft 108, along with first jaw 120A and second jaw 120B, can be rotated a full 360 degrees, as shown by arrow 117, relative to handle 105 through, for example, a rotary triple contact. First jaw 120A and second jaw 120B can remain openable and/or closeable while rotated.

Figure 4:
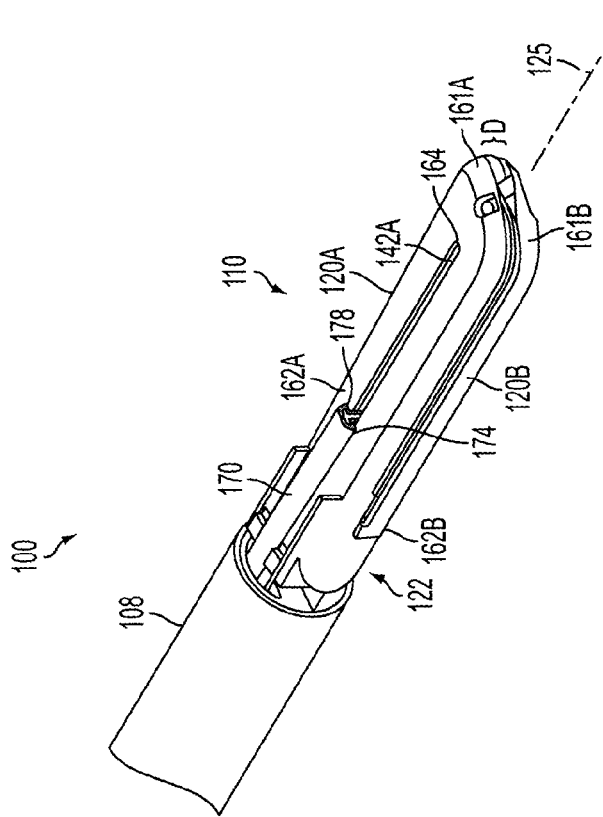
FIG. 4 is a perspective view of the end effector of the surgical instrument of FIG. 1 illustrated in a closed configuration; the distal end of the closure beam is illustrated in a partially advanced position.
Figure 3:
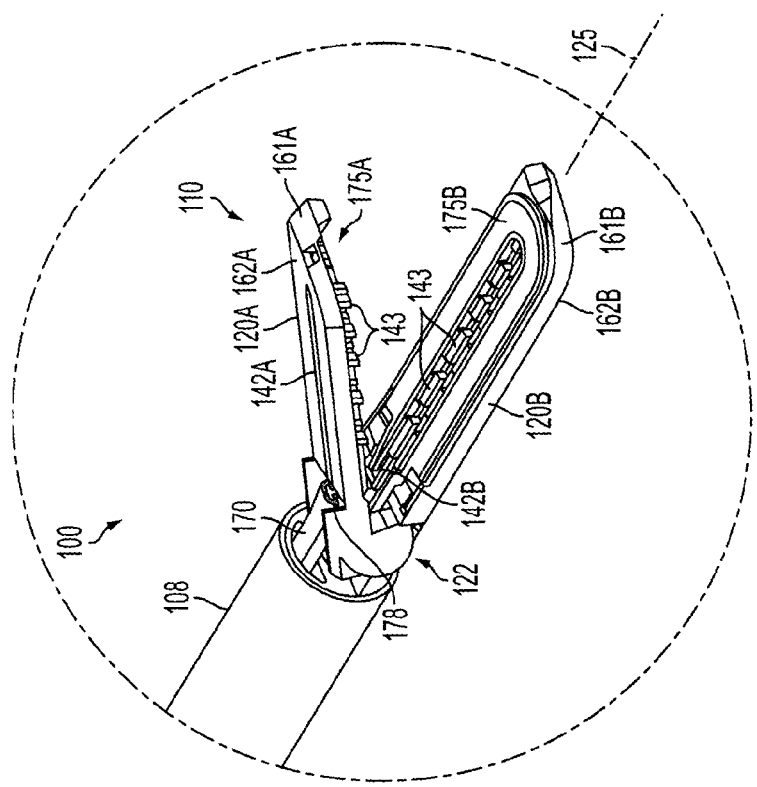
FIG. 3 is a perspective view of an end effector of the surgical instrument of FIG. 1 illustrated in an open configuration; the distal end of a closure beam is illustrated in a retracted position.

FIGS. 3 and 4 illustrate perspective views of end effector 110. FIG. 3 shows end effector 110 in an open configuration and FIG. 4 shows end effector 110 in a closed configuration. As noted above, the end effector 110 may comprise the upper first jaw 120A and the lower second jaw 120B. Further, the first jaw 120A and second jaw 120B may each have tissue-gripping elements, such as teeth 143, disposed on the inner portions of first jaw 120A and second jaw 120B. First jaw 120A may comprise an upper first jaw body 161A with an upper first outward-facing surface 162A and an upper first energy delivery surface 175A of a first electrode, for example. Second jaw 120B may comprise a lower second jaw body 161B with a lower second outward-facing surface 162B and a lower second energy delivery surface 175B of a second electrode, for example. First energy delivery surface 175A and second energy delivery surface 175B may both extend in a "U" shape about the distal end of end effector 110. The energy delivery surfaces 175A, 175B may provide a tissue contacting surface or surfaces for contacting, gripping, and/or manipulating tissue therebetween.

Referring to FIGS. 3-5, in at least one embodiment, the closure beam 170 and the cutting member 140 may be sized and configured to fit at least partially within the channel 142A of the first jaw 120A. As seen in FIG. 5, the cutting member 140 may also be sized and configured to fit at least partially within the channel 142B of the second jaw 120B. In any event, the closure beam 170 and the cutting member 140 may translate along the channel 142A between a first, retracted position correlating with the first jaw being at the open position (FIG. 3), and a second, advanced position correlating with the second jaw being at the closed position (see, for example, FIG. 4). The trigger 128 of handle 105, see FIG. 2, may be adapted to actuate cutting member 140 and, subsequently, closure beam 170, which also functions as a jaw-closing mechanism. For example, cutting member 140 and/or closure beam 170 may be urged distally as trigger 128 is pulled proximally along path 129 via shuttle 146, seen in FIG. 2 and discussed above. The cutting member 140 and closure beam 170 may each comprise one or several pieces, but in any event, may each be movable or translatable with respect to the elongate shaft 108 and/or jaws 120A, 120B. Also, in at least one embodiment, the cutting member 140 may be made of 17-4 precipitation hardened stainless steel. The distal portion of cutting member 140 may comprise a flanged "I"-beam configured to slide within channels 142A and 142B in jaws 120A and 120B. In at least one embodiment, the distal portion of closure beam 170 may comprise a "C"-shaped beam configured to slide within one of channels 142A and 142B. As illustrated in FIGS. 3-5, the closure beam is shown residing in and/or on channel 142A of the first jaw 120A. Closure beam 170 may slide within channel 142A, for example, to open and close first jaw 120A with respect to second jaw 120B. The distal portion of closure beam 170 may also define inner cam surfaces 174 for engaging outward facing surfaces 162A of the first jaw 120A, for example. Accordingly, as the closure beam 170 is advanced distally through the channel 142A, from, for example, a first position (FIG. 3) to a second position (FIG. 4), the first jaw 120A may be urged closed (FIG. 4). The closure beam may also be guided by upper walls 165 of the first jaw 120A, which as seen in FIG. 5 may at least partially envelope the closure beam 170. The upper walls 165 have been omitted from FIGS. 3-4 for purposes of clarity.

Additionally, in various embodiments, the cutting member 140 may be sized and configured to at least partially fit or slide within the closure beam 170, such as within an inner channel 171 of the closure beam 170, for example. In at least one embodiment, as seen in FIG. 5, while part of the cutting member 140 may be positioned within the closure beam 170, a portion of the cutting member 140 may protrude from the closure beam 170 in a direction transverse to a longitudinal axis 172 defined by the closure beam 170. The flanges 144A and 144B of cutting member 140 may define inner cam surfaces for engaging the inner channel 171 of the closure beam 170 and the outward facing surfaces 162B of the second jaw 120B. As discussed in greater detail below, the opening and closing of jaws 120A and 120B can apply very high compressive forces on tissue using cam mechanisms which may include reciprocating "C-beam" closure beam 170 and/or "I-beam" cutting member 140 and the outward facing surfaces 162A, 162B of jaws 120A, 120B.

More specifically, referring still to FIGS. 3-5, collectively, flanges 144A and 144B of the distal end of cutting member 140 may be adapted to slidably engage the inner channel 171 of the closure beam 170 and the second outward-facing surface 162B of the second jaw 120B, respectively. Channel 142A within first jaw 120A and channel 142B within second jaw 120B may be sized and configured to accommodate the movement of closure beam 170 and/or cutting member 140, which may comprise a tissue-cutting element, for example, a sharp distal edge and/or surface 153 (see FIG. 6). FIG. 4, for example, shows the distal end 178 of the closure beam 170 advanced at least partially through channel 142A. The advancement of the closure beam 170 can close the end effector 110 from the open configuration shown in FIG. 3 to the closed configuration shown in FIG. 4. The closure beam 170 may move or translate along the channel 142A between a first, retracted position and a second, fully advanced position. The retracted position can be seen in FIG. 3, where the jaws 120A, 120B are in an open position and a distal end 178 of the closure beam 170 is positioned proximal to the upper outward-facing surface 162A. The fully advanced position, while not shown, may occur when the distal end 178 of the closure beam 170 is advanced to a distal end 164 of channel 142A and the jaws are in a closed position, see FIG. 4. Likewise, the cutting member 140 (FIG. 5) may be configured to translate with respect to the first jaw between a retracted position, where the jaws 120A, 120B are in an open position (FIG. 3) and a fully advanced position where the cutting member is advanced to the distal end 164 of the channel 142A, for example, with the jaws in a closed position (FIG. 4). As noted above, the cutting member 140 may also translate with respect to the closure beam 170 as the closure beam 170 is being advanced through the jaws 120A, 120B. At a point, however, the cutting member 140 may be decoupled from the closure beam 170 as discussed in more detail below. Accordingly, the advancing of the closure beam 170 may apply an initial, lower level or amount of compression pressure or force to tissue gripped between the jaws 120A, 120B and subsequent advancing of the cutting member 140 relative to the closure beam 170, as discussed below, may not only cut or sever tissue, but may also apply a higher level or amount of compression pressure or force to tissue gripped between the jaws 120A, 120B. The higher level or amount of compression provided by the cutting member 140 to gripped tissue may be due to the fact that the closure beam 170 may only apply force to the first jaw 120A, whereas the cutting member 140 may apply force to both jaws 120A and 120B. The lower level or amount of compression may be desirable when tissue is only being manipulated, whereas the higher level or amount of compression may be desirable when tissue is being energetically sealed and/or transected.

In at least one embodiment, distal portions of the closure beam 170 and the cutting member 140 may be positioned within and/or adjacent to one or both of jaws 120A and 120B of the end effector 110 and/or distal to the elongate shaft 108. More specifically, referring to FIG. 5, a plane that is perpendicular to the cutting member's longitudinal axis 125, such as the plane cross-sectioning the end effector 110 in FIG. 5, for example, may transect the closure beam 170, the cutting member 140, and a tissue contacting surface of the first jaw 120A, such as energy delivery surface 175A, for example, when closure beam 170 is at a second, fully advanced position and the cutting member 140 is also at its fully advanced position. Such a plane may also transect a tissue contacting surface of the second jaw 120B, such as energy delivery surface 175B, for example, likewise when the closure beam 170 is at a second, fully advanced position and the cutting member is also at its fully advanced position.

Further, in the closed position shown by FIG. 4, upper first jaw 120A and lower second jaw 120B define a gap or dimension D between the first energy delivery surface 175A and second energy delivery surface 175B of first jaw 120A and second jaw 120B, respectively. Dimension D may equal from about 0.0005" to about 0.040", for example, and preferably between about 0.001" to about 0.010", for example. Also, the edges of first energy delivery surface 175A and second energy delivery surface 175B may be rounded to prevent the dissection of tissue.

Referring now to FIGS. 1 and 3, end effector 110 may be coupled to electrical source 145 and controller 150. First energy delivery surface 175A and second energy delivery surface 175B may likewise each be coupled to electrical source 145 and controller 150. First energy delivery surface 175A and second energy delivery surface 175B may be configured to contact tissue and deliver electrosurgical energy to engaged tissue which is adapted to seal or weld the tissue. Controller 150 can regulate the electrical energy delivered by electrical source 145 which in turn delivers electrosurgical energy to first energy-delivery surface 175A and second energy-delivery surface 175B. The energy delivery may be initiated by an activation button 124 operably engaged with trigger 128 and in electrical communication with controller 150 via cable 152. As mentioned above, the electrosurgical energy delivered by electrical source 145 may comprise radiofrequency (RF) energy. Further, the opposing first and second energy delivery surfaces 175A and 175B may carry variable resistive positive temperature coefficient (PTC) bodies that are coupled to electrical source 145 and controller 150. Additional details regarding electrosurgical end effectors, jaw closing mechanisms, and electrosurgical energy-delivery surfaces are described in the following U.S. patents and published patent applications, all of which are incorporated herein in their entirety by reference and made a part of this specification: U.S. Pat. Nos. 7,381,209; 7,311,709; 7,220,951; 7,189,233; 7,186,253; 7,125,409; 7,112,201; 7,087,054; 7,083,619; 7,070,597; 7,041,102; 7,011,657; 6,929,644; 6,926,716; 6,913,579; 6,905,497; 6,802,843; 6,770,072; 6,656,177; 6,533,784; and 6,500,176; and U.S. Pat. App. Pub. Nos. 2010/0036370 and 2009/0076506.

Figure 6:
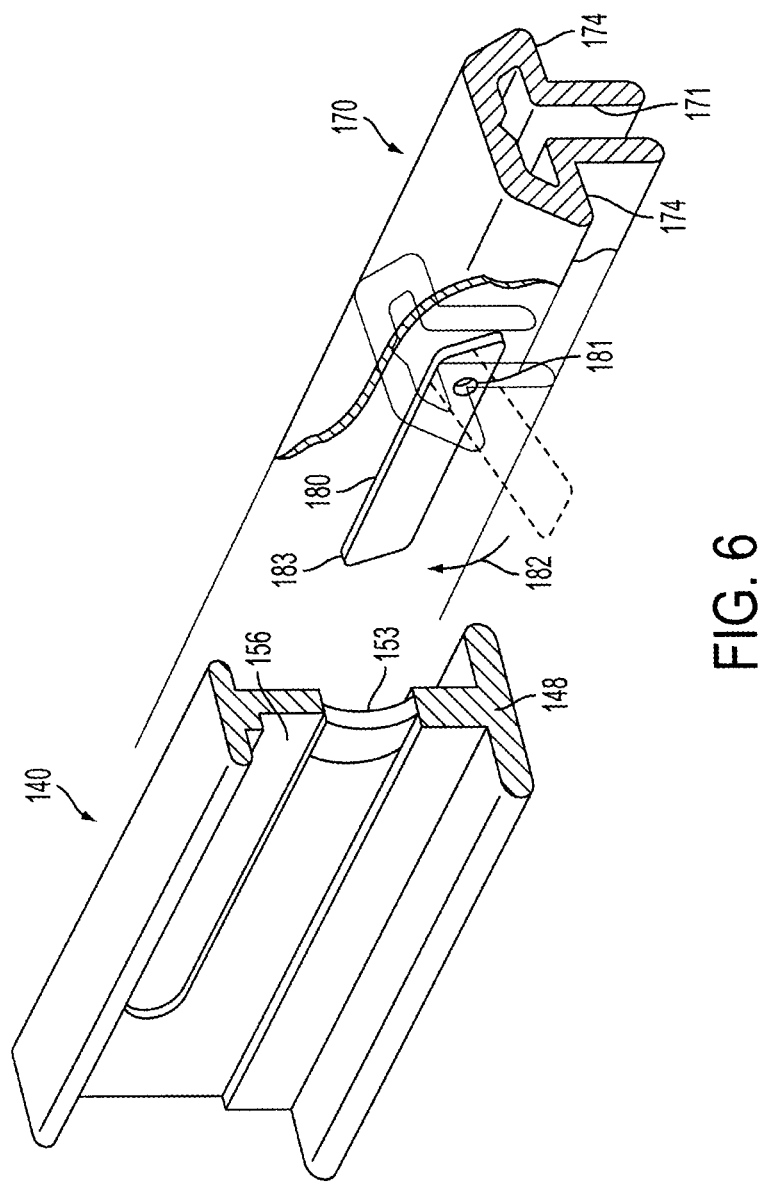
FIG. 6 is a perspective sectional view of portions of a cutting member and a closure beam of a surgical instrument of the surgical instrument of FIG. 1.

In various embodiments, it may be desirable to close the jaws 120A, 120B, before advancing the cutting member 140 therethrough. Accordingly, referring to FIGS. 3-5, the closure beam 170 may be advanced at least partially through the channel 142A prior to the cutting member 140 being advanced into the channel 142A. In such embodiments, an interlocking member may selectively hold the cutting member 140 and the closure beam 170 together such that they translate synchronously with each other in at least one direction with respect to the first jaw until the interlocking member decouples the cutting member 140 from the closure beam 170, after which the cutting member 140 may be advanced through the channels 142A, 142B in jaws 120A, 120B and/or through the closure beam 170. In at least one embodiment, referring to FIG. 6, the interlocking member may comprise a pawl, such as pawl 180, rotatably mounted to the closure beam 170 or to the cutting member 140. As illustrated in FIG. 6, the pawl may be rotatably mounted to at least one inner surface of the closure beam channel 171 at a hole 181 in the pawl 180. The pawl 180 may be rotatable between a first, locked position (shown in phantom lines in FIG. 6) and a second, unlocked position (shown in solid lines in FIG. 6). A biasing member (not shown), such as a torsion spring, for example, may bias the pawl in the direction of arrow 182, towards the unlocked position. As will be explained in more detail below, a proximal end 183 of the pawl 180 may be configured to engage various portions of the cutting member 140. For example, in at least one embodiment, the distal end 148 of the cutting member 140 may be engaged by the proximal end 183 of the pawl 180 when the pawl 180 is in the locked position. Additionally, in at least one embodiment, the proximal end 183 of the pawl 180 may be slidably received in a recess 156 formed in the cutting member 140 when the pawl 180 is in the unlocked position.

The pawl 180 may selectively interconnect the cutting member 140 and the closure beam 170 as follows. Referring to FIGS. 7 and 8, the closure beam 170 may be advanced from a retracted, initial position (FIG. 7) to a fully advanced position (FIG. 8) when a user pulls the trigger 128 (see FIGS. 1-2) towards the handle body 106A or 106B. Pulling on the trigger 128 in such a fashion moves the cutting member 140 distally and, as a result, the closure beam 170 may likewise be moved distally owing to the pawl's proximal end 183 being forced in a distal direction by the cutting member's distal end 148. Friction and/or interference between the pawl's proximal end 183 and the cutting member's distal end 148 may hold the pawl 180 in its locked position when the cutting member 140 is still or moving distally. After advancing the closure beam 170 to close the jaws 120A, 120B (FIG. 8), the cutting member 140 may be advanced relative to the closure beam 170. A user may be provided with feedback, such as haptic feedback (discussed in more detail below), for example, when the closure beam 170 is stopped from moving distally by the distal end 164 of the first jaw's channel 142A (see FIG. 4). To unlock the pawl 180, a user may move, or return, the trigger 128 (FIGS. 1-2) slightly away from the handle body 106A and/or 106B. Referring to FIG. 9, moving the trigger 128 in such a manner may move the cutting member 140 proximally such that the pawl 180 may be released from its locked position (phantom lines in FIG. 9) and rotate to its unlocked position (solid lines) in the direction of arrow 182 owing to the presence of the biasing member (not shown). After the pawl 180 is in its unlocked position, the cutting member 140 may be advanced by a user by moving the trigger back towards the handle body 106A and/or 106B once again. The cutting member 140 may now move into and/or through the jaws 120A and 120B independently of closure beam 170 because the pawl 180 may slide into the cutting member recess 156.

Alternative pawl configurations are also possible. For example, referring now to FIG. 10, a distal portion of a surgical instrument 200 is illustrated gripping tissue T; various portions of the illustrated instrument 200 have been omitted for clarity. The surgical instrument 200 may be generally similar to surgical instrument 100 described above. For example, the surgical instrument 200 may comprise a handle 105 (FIG. 1) operably coupled to an end effector 210 by an elongate shaft 108. The end effector 210 may comprise openable and closable jaws 220A and 220B that are closed by the relative advancement of a closure beam 270 driven by a cutting member 240. The cutting member 240 may be moved relative to the jaws 220A, 220B when a user moves a trigger, which can be similar to trigger 128 (see FIGS. 1-2), relative to a handle body, which can be similar to handle bodies 106A and/or 106B (see FIGS. 1-2). The cutting member 240 and the closure beam 270 may be selectively held together or interlocked by an interlocking member, such as pawl 280 rotatably or pivotably mounted to an inner portion of the closure beam 270, for example. Additionally, referring to FIG. 11, the pawl 280 may be rotatably as well as translatably mounted to the closure beam 270 by a pawl pin 285 received in an arcuate slot 284 of the closure beam 270. A biasing member (not shown) may bias the spring towards a neutral position as shown in FIG. 11. The pawl 280 may rotate in the direction indicated by arrow 286, away from the closure beam 270, or the pawl 280 may rotate in the direction indicated by arrow 287, toward the closure beam 270; however, in the absence of an external force on the pawl 280, the pawl 280 may be biased toward the neutral position seen in FIG. 11. An indentation 221 formed in inner surface of first jaw 220A may facilitate the pawl 285 in translating along the slot 284 when the pawl 280 is positioned adjacent to the indentation 221.

Figure 10:
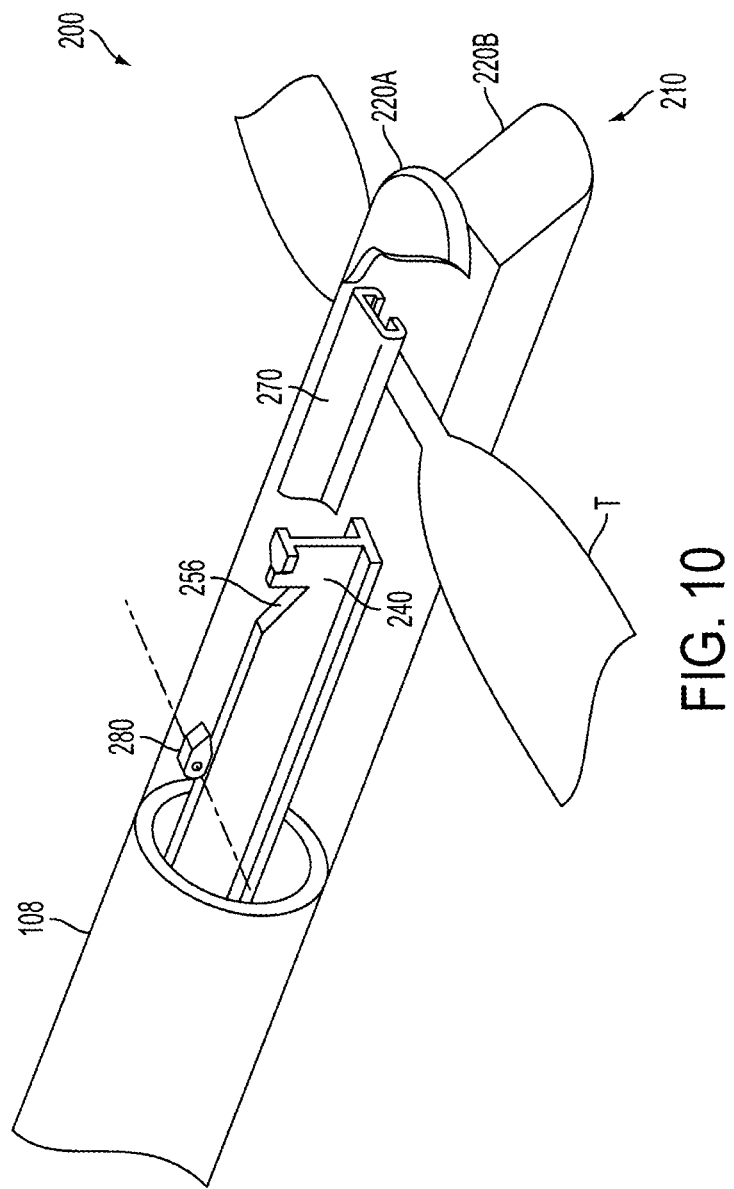
FIG. 10 is a perspective cut-away view of a distal portion of a surgical instrument gripping tissue according to a non-limiting embodiment; various internal components are shown and some components have been omitted for clarity.

The pawl 280 may selectively hold the closure beam 270 and the cutting beam together at least partially due to friction between the pawl 280 and the cutting member 240. Accordingly, when the pawl is at the neutral position seen in FIG. 11, sufficient friction and/or interference may exist between the pawl 280 and the closure beam's distal end 248 such that the closure beam 270 may be advanced by the cutting member 240 at least partially through the first jaw 220A (FIG. 10) such that the jaw 220A at least partially closes. After or while closing the jaws 220A, 220B, the closure beam 270 may experience sufficient resistive forces, such as from gripping tissue, for example, that may allow the pawl to rotate to a collapsed position such as that shown in FIG. 12, for example. Continued advancement of the cutting member 240 in a distal direction, such as that indicated by arrow "D" in FIG. 12, for example, may still advance the closure beam 270 in the distal direction D due to sufficient friction between the outer surfaces of the biased pawl 280 and the cutting member 240. However, after the closure beam 270 reaches the distal end of the jaw's channel (not shown, see the channel's distal end 164 in FIG. 4, for example), the cutting member 240 may then be advanced further relative to both the closure beam 270 and the jaws 220A, 220B (FIG. 10). In such situations, the resistive friction forces between the pawl 280 and the cutting member 240 may be overcome such that the cutting member 240 slides relatively against the pawl 280. Referring to FIG. 13, the cutting member 240 may be retracted in a proximal direction, such as that indicated by arrow "P," for example, until the pawl 280 is forced into an extended position in a recess 256 of the cutting member 240, thereby interconnecting the closure beam 280 to the cutting member 240 for retracting the cutting member 240 and the closure beam 280 from the jaws 220A, 220B (FIG. 10). After the closure beam 270 has been sufficiently retracted, the jaws may open.

Figure 14:
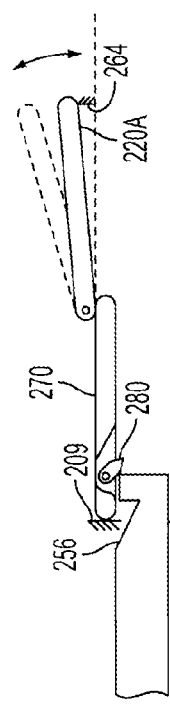
FIGS. 14-21 are schematic side views of the jaw, the closure beam, the pawl, and a distal portion of the cutting member of the surgical instrument of FIG. 10 in various configurations to illustrate the interaction between and operation of the above-listed components.
Figure 15:
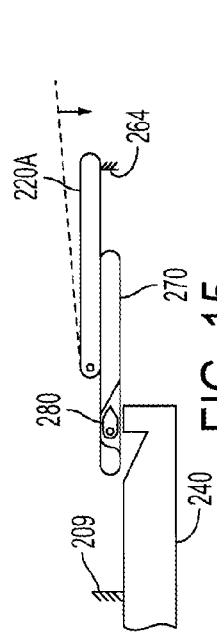
Figure 16:
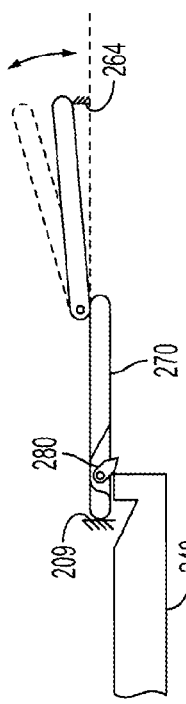

FIGS. 14-21 provide a schematic set of diagrams that further illustrate the operation of the pawl 280, a distal portion of the cutting member 240, the closure beam 270, and the jaw 220A; other components have been omitted for clarity. As shown in FIG. 14, the closure beam is in a retracted, resting position. As the cutting member 240 is advanced distally, toward the jaw 220A, the closure beam 270 may likewise be advanced owing to friction and/or interference between the pawl 280 and the cutting member 240. As the closure beam 270 is advanced into, through, and/or adjacent to the jaw 220A, the jaw 220A may be urged into a closed position such as that shown in FIG. 15. As seen in FIG. 15, the pawl has already been rotated to a collapsed position by the advancement of the cutting member 240 relative to the jaw 220A and/or the closure beam 270. However, sufficient friction may exist between the biased pawl 280 and the cutting member 240 such that the closure beam 270 and the cutting member 240 may still be translationally interconnected or interlocked. Accordingly, as seen in FIG. 16, the jaw 220A may be reopened by retracting the cutting member 240 in a proximal direction, away from the jaw 220A such that the closure beam 270 also retracts proximally Retracting the cutting member 240 in such a fashion may likewise cause the closure beam 270 to retract distally, until the closure beam 270 reaches a stop 209 positioned inside the elongate shaft 108 (FIG. 11), for example. Referring still to FIG. 16, after the closure beam 270 reaches the stop 209, the cutting member 240 may thereafter slide along the pawl 280, until the pawl 280 at least partially clears the cutting member 240 such that the pawl 280 is forced to rotate to its neutral position by the biasing member (not shown). The cutting member 240, referring to FIG. 17, may thereafter be re-advanced, thereby also re-advancing the closure beam 270 and re-closing the jaw 220A.

Figure 17:
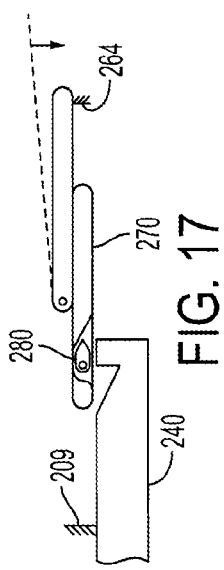
Figure 18:
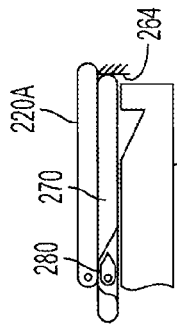

After the jaw 220A has been closed by the closure beam 270 as seen in FIG. 17, for example, the cutting member 240 may continue to be advanced distally, thereby also advancing the closure beam 270 due to friction between the pawl 280 and the cutting member 240. Referring to FIG. 18, once the closure beam 270 reaches the jaw's channel's distal end 264 (see also the distal end 164 of channel 142A in FIG. 4), the cutting member 240 may begin to be slide along the pawl 280 and be advanced through the jaws 220A and/or 220B and any tissue T gripped therebetween (see FIG. 10) until the cutting member 240 reaches a fully advanced position or another desired position.

Figure 19:
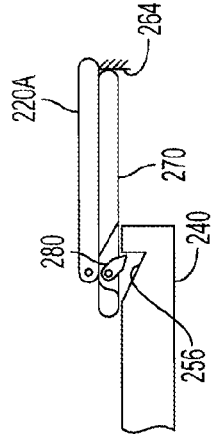
Figure 20:
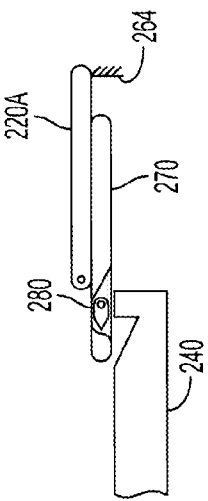
Figure 21:
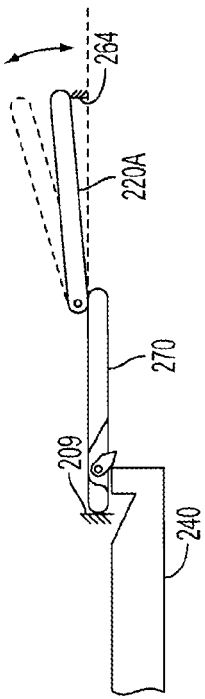

The closure beam may be retracted from the jaw 220A and the jaw 220A may be reopened after advancing the cutting member 240 into the jaw 220A as follows. Referring to FIG. 19, the cutting member 240 may be retracted in a proximal direction, away from channel distal end 264. However, owing to resistive friction from tissue recently cut by and/or potentially still contacting the sides of the cutting member 240, friction between the pawl 280 and the cutting member 240 may no longer be sufficient to interlock the closure beam 270 and cutting member translationally together. Thus, as the cutting member is retracted, the pawl 280 may be biased into the recess 256 of the cutting member 240, thereby serving as a catch and holding the cutting member 240 and the closure beam 270 together by way of interference between the pawl 280 and the recess 256. Accordingly, further retraction of cutting member 240 in a proximal direction, i.e., away from the channel distal end 264, may begin moving the closure beam 270 in a proximal direction also. As shown in FIGS. 10-21, the recess 256 may be positioned proximate or close to the distal end of the cutting member 240. However, alternatively, the recess may be positioned farther away from the distal end of the cutting member 240 than shown. For example, in one embodiment, the recess 256 may be positioned relative to the jaw 220A such that the pawl 280 may be received in the recess 256 when the cutting member 240 reaches a fully advanced position (see FIG. 18). Accordingly, in such embodiments, the pawl 280 may help hold the cutting member 240 and the closure beam 270 together immediately after the cutting member 240 is fully advanced and/or during the cutting member's retraction. In any event, referring to FIG. 20 and in at least one embodiment, after the closure beam 270 has been at least partially retracted, the pawl 280 may rotate and translate into another collapsed position owing to the arcuate slot 284 seen in FIGS. 11-13. Referring to FIG. 21, such movement of the pawl 280 may allow the cutting member 240 to be fully retracted to the position seen in FIG. 21, after which the pawl 280 may reset and be biased to its neutral position by the biasing member (not shown). Alternatively, in at least one embodiment, the pawl 280 may return to the neutral position seen in FIG. 11 from the extended position shown in FIG. 13 by a user moving, or pulling on, the trigger 128 (FIGS. 1-2) slightly toward from the handle body 106A and/or 106B such that the cutting member 240 and recess 256 move distally, thereby allowing the pawl 280 to rotate to a collapsed position, within the closure beam 270 (see FIG. 12). Subsequently, a user may move, or return, the trigger 128 (FIGS. 1-2) more fully away from the handle body 106A and/or 106B such that the pawl 280 may return to its neutral position, thereby resetting the pawl 280. In any event, thereafter, the above steps and/or relative movements represented in one or more of FIGS. 14-21 may be repeated to again grasp, manipulate, and/or cut tissue, for example.

Additional details of pawl configurations which may serve as an interlocking member according to various embodiments may be found in U.S. patent application Ser. No. 11/076,612, entitled MRI BIOPSY DEVICE, the disclosure of which is incorporated by reference herein in its entirety.

Figure 22:
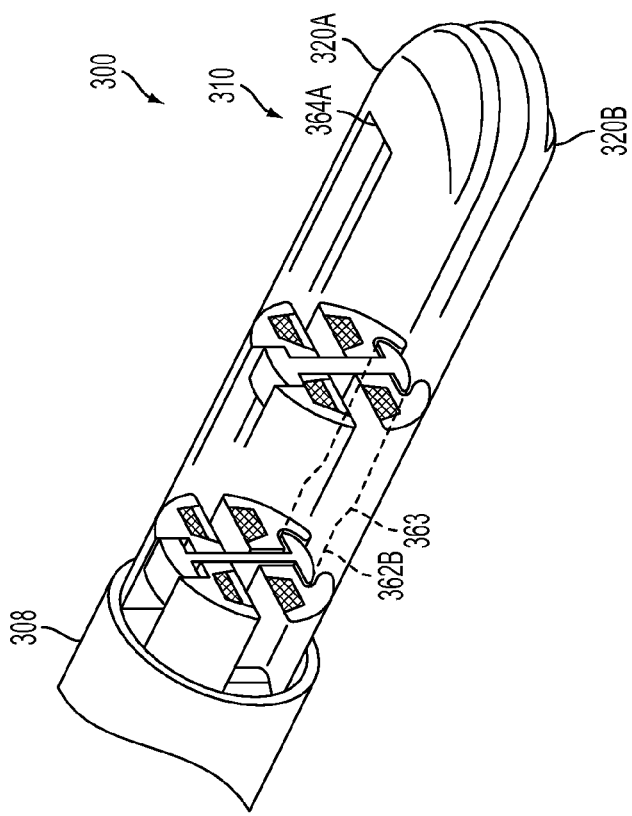
FIG. 22 is a perspective view of a distal portion of a surgical instrument according to a non-limiting embodiment; various internal components are shown in perspective sectional form and some components are omitted for the purposes of clarity.

In at least one embodiment, the interlocking member may comprise a nub protruding from the cutting member. For example, referring to FIGS. 22-23, a surgical instrument 300, generally similar to surgical instrument 100 described above, may comprise an end effector 310 and a handle (not shown, see handle 105 in FIG. 1) operably coupled together by an elongate shaft 308. The end effector 310 may comprise openable and closable jaws 320A and 320B that are closed by the relative advancement of a closure beam 370 (not shown for clarity in FIG. 22, see FIG. 23) driven by a cutting member 340. The cutting member 340 may be moved relative to the jaws 320A, 320B, when a user moves a trigger, which can be similar to trigger 128 (see FIGS. 1-2) relative to a handle body, which can be similar to handle bodies 106A and/or 106B (see FIGS. 1-2). The cutting member 340 and the closure beam 370 may be selectively held together or interlocked by an interlocking member, such as a nub 380 protruding from the top or outer portion of the cutting member 340, for example. The nub 380 may be unitary and integrally formed with the cutting member 340. Alternatively, the nub 380 may be attached to the cutting member by an adhesive, a weld, a fastening member, and/or any other suitable type of attachment mechanism, for example.

Figure 23:
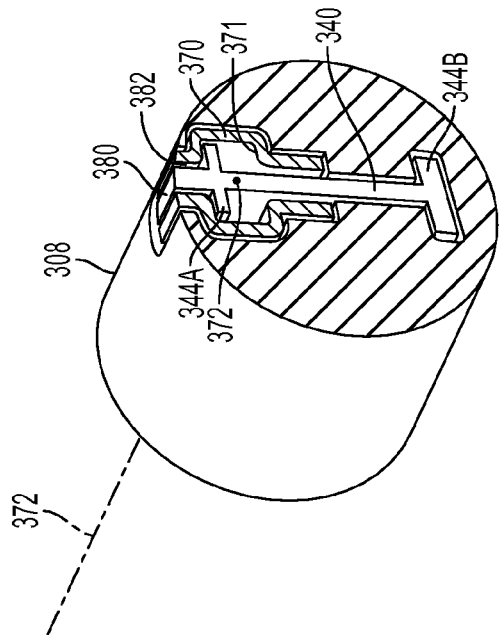
FIG. 23 is a perspective sectional view of a portion of an elongate shaft, a closure beam, a cutting member, and a nub of the surgical instrument of FIG. 22.

As seen in FIG. 23, the nub 380 may be configured to engage the closure beam 370 when the cutting member 340 is at a raised position relative to the closure beam 370. In such embodiments, the nub 380 may engage, nest in, and/or be otherwise releasably received by a notch or detent 382 formed in the inner channel 371 of the closure beam 370. The detent 382 may comprise a proximal wall and a distal wall (not shown) that allow the closure beam 370 to be translationally coupled to the cutting member 340 when the cutting member 340, and hence the nub 380, are at the raised position. Alternatively, although not illustrated, in at least one embodiment, the nub 380 may be attached and/or formed in the closure beam 370 and the detent 382 may be formed in the cutting member 340.

Figure 24:
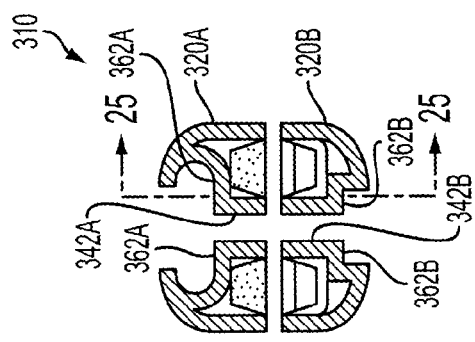
FIG. 24 is a cross-sectional view of jaws of the surgical instrument of FIG. 22, taken transverse to a longitudinal axis of the jaws.
Figure 25:
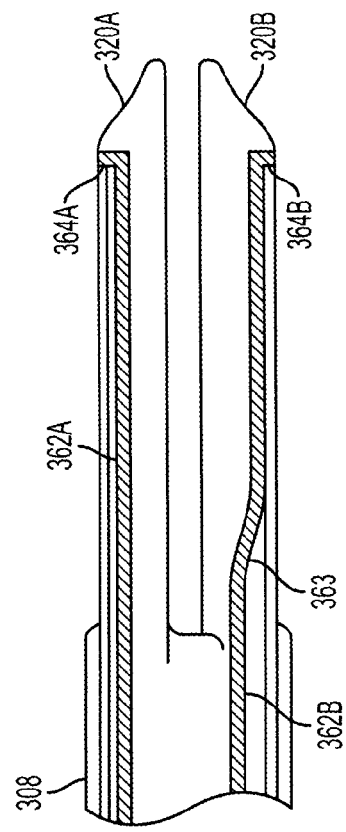
FIG. 25 is a cross-sectional view of the jaws and a portion of the elongate shaft of the surgical instrument of FIG. 22, taken along line 25-25 in FIG. 24.
Figure 26:
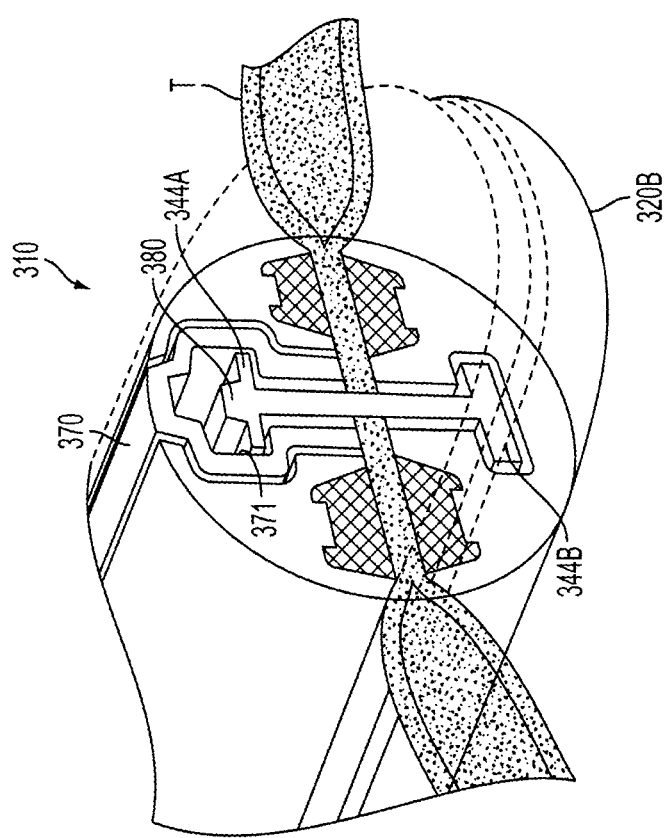
FIG. 26 is a perspective view of a distal portion of an end effector of the surgical instrument of FIG. 22; the end effector is shown gripping, sealing, and/or cutting tissue.

The nub 380 may be disengaged from the detent 382 when the closure beam 370 is at a desired position, such as a fully advanced position, relative to the jaw 320A. Referring now to FIGS. 24-26, the second jaw 320B may comprise an outward facing surface 362B. The outward facing surface 362B may guide the lower flanges 344B of the cutting member 340 (FIG. 23) such that the cutting member moves transverse to the closure beam's longitudinal axis 372 (FIG. 23). As seen in FIG. 25, the outward facing surface 362B may further comprise at least one ramped surface 363. The ramped surface 363 may contact at least a portion of the cutting member, such as lower flanges 344B, for example, to cause the cutting member 340, and hence the nub 380, to move from the raised position seen in FIG. 23, to a lowered position as illustrated in FIG. 26, for example, when the cutting member 340 is advanced in a distal direction. In other words, the cutting member 340 and the nub 380 may be moved transverse to the closure beam's longitudinal axis 372 (FIG. 23) as the lower flanges 344B of cutting member 340 are advanced distally along the ramped surface 363. In such a lowered position (FIG. 26), the nub 380 may be disengaged from the detent 382 of the closure beam 370. The cutting member 340 may thus move relative to the jaws 320A, 320B and to the closure beam 370. In other words, when the nub 380 is at the lowered position, the cutting member 340 may move independently from the closure beam 370, without affecting the latter's position relative to the jaws 320A, 320B. Likewise, as the cutting member 340 is retracted in a proximal direction, the ramped surface 363 may cause the cutting member 340 and the nub 380 to move back to the raised position, thereby interlocking the closure beam 370 and the cutting member 340 via the interface between the nub 380 and the detent 382. Further, the upper cutting member flanges 344A may move within the closure beam 370 as the cutting member 340 translates between the raised and lowered positions such that the flanges 344A contact and/or press against the inner surfaces of the closure beam 370 when the cutting member is at the lowered position.

Figure 27:
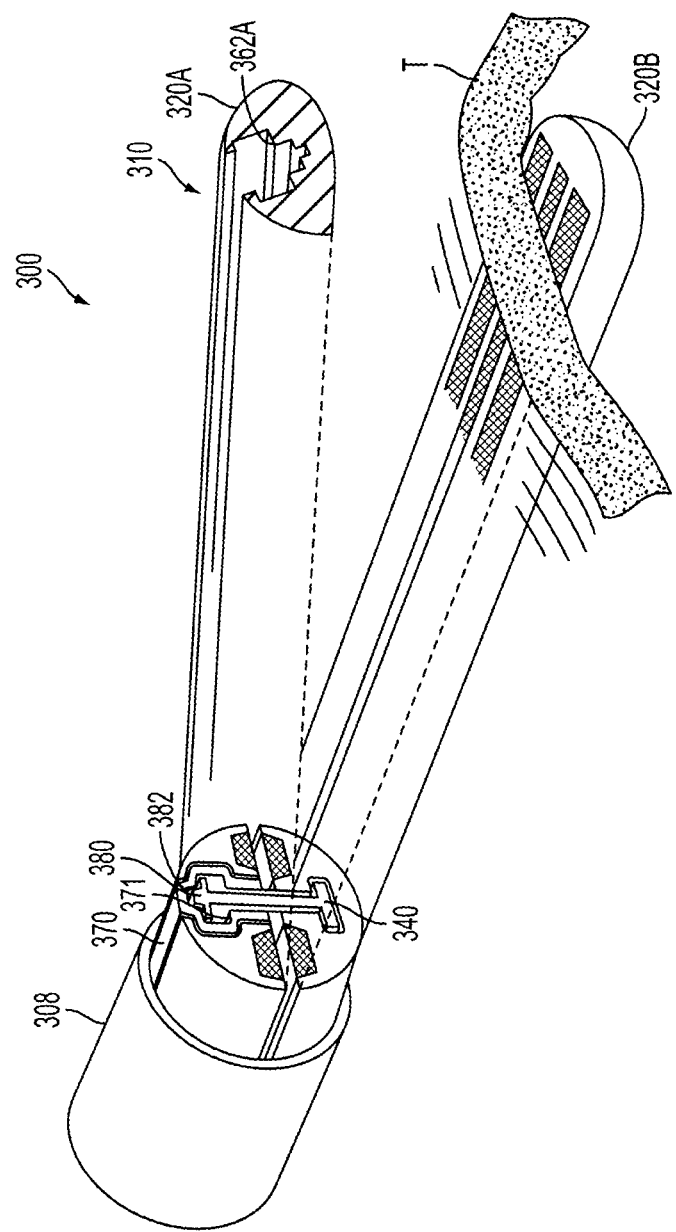
FIG. 27 is a perspective view of a distal portion of the surgical instrument of FIG. 22 with the jaws in an open configuration and the closure beam and the cutting member in a retracted position; various internal components are shown in perspective sectional form for the purposes of clarity.
Figure 28:
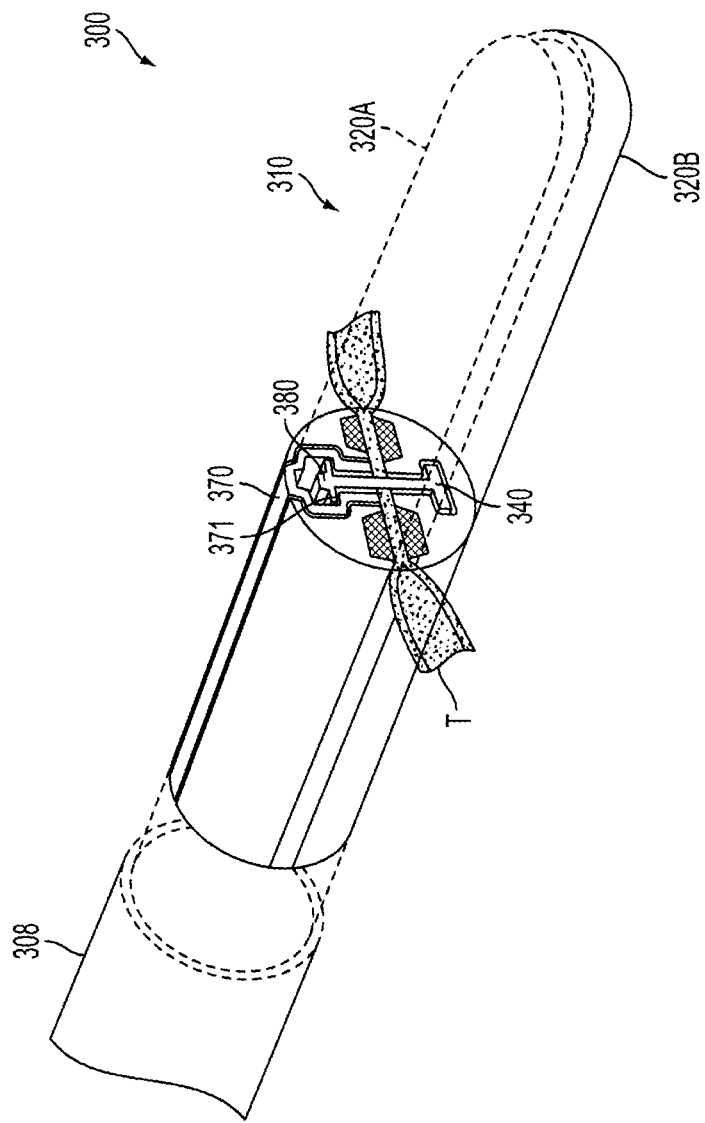
FIG. 28 is a perspective view of a distal portion of the surgical instrument of FIG. 22 with the jaws in a closed configuration and the closure beam and/or cutting member at least partially advanced through the jaws; various internal components are shown in perspective sectional form for the purposes of clarity.

Referring to FIGS. 27-28, the surgical instrument 300 may be operated as follows. The first jaw 320A may be rotated from an open position (FIG. 27) to a closed position (FIG. 28) as the cutting member 340 and the closure beam 370 are advanced synchronously due to the nub 380 being positioned within the detent 382, thereby interlocking the cutting member 340 and the closure beam 370. The closure beam 370 may be advanced through the end effector 310, along the first jaw's outward facing surface 362A, and ahead of the cutting member 340, until the closure beam 370 reaches the distal end 364A (see FIG. 25) of the first jaw's channel 342A (FIG. 24) or another predetermined position. At or about the same time, the lower flanges 344B of the cutting member 340 may encounter the ramped surface 363 (FIG. 25) which may cause the cutting member 340 and the nub 380 to move from the raised position (FIG. 27) to the lowered position (FIG. 28) relative to the closure beam 370. Thereafter, because the nub 380 may no longer be positioned within the detent 382, the cutting member 340 may be advanced distally independent of the closure beam 370, thereby severing tissue "T," in the process.

In various embodiments described above, a trigger, such as trigger 128 seen in FIGS. 1-2, may be configured to actuate a cutting member, such as cutting member 140, 240, and/or 340, and a closure beam, such as closure beam 170, 270, and/or 370, for example, such that the closure beam and the cutting member translate with respect to a first jaw, such as jaw 120A, 220A, and/or 320A, for example. Such actuation of both the closure beam and the cutting member may provide a user with the ability to control the closing of the jaw(s) and the firing of the cutting member through the jaw(s) by only using one trigger. In such embodiments, a handle trigger may be configured to provide haptic feedback to a user such that the user is provided with feedback as to where the surgical instrument is in the closing, sealing, and/or cutting stages.

Figure 29:
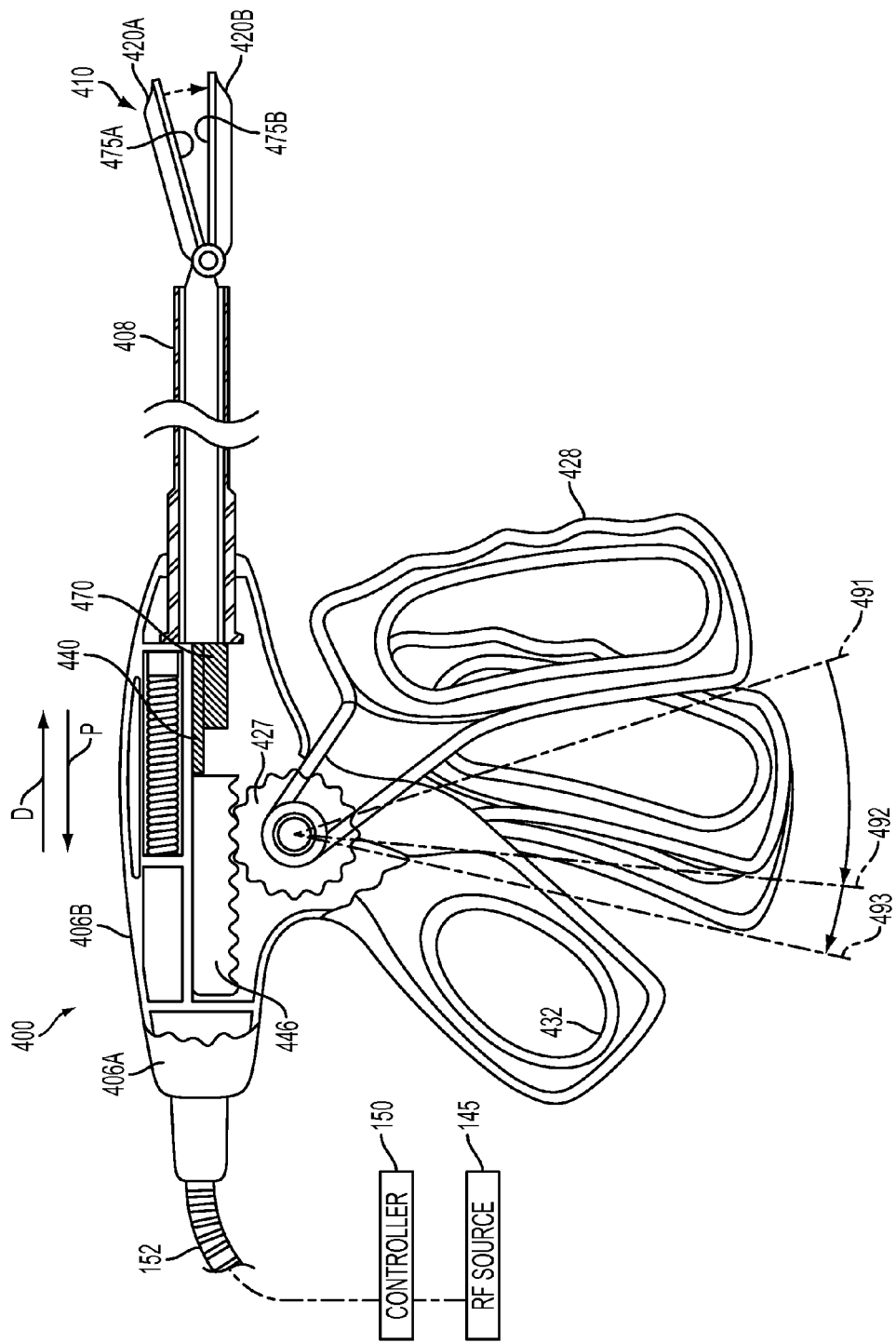
FIG. 29 is a side view of a surgical instrument according to a non-limiting embodiment; various portions of the instrument are cut away and/or shown in cross-sectional form for the purposes of clarity.

Referring now to FIG. 29, a simplified illustration of a surgical instrument 400 is shown. A portion of the handle body 406B is cut away to show some of the inner components positioned inside the handle body 406A of the handle. The surgical instrument 400 may be generally similar to surgical instrument 100 described above. For example, as seen in FIG. 29, the surgical instrument 400 may comprise a handle operably coupled to an end effector 410 by an elongate shaft 408. The end effector 410 may comprise openable and closable jaws 420A and 420B that are closed by the relative advancement of a closure beam 470 driven by a cutting member 440. The cutting member 440 may be moved relative to the jaws 420A, 420B, when a user moves a trigger, such as trigger 428, for example, relative to a thumb rest 432 formed in handle bodies 406A and/or 406B. The cutting member 440 may be selectively interlocked with a closure beam 470 by one or more of the interlocking members described above. Additionally, in at least one embodiment, the interlocking member(s) may be positioned within the handle and/or proximal to the elongate shaft 408 at least initially, prior to closing the jaws 420A, 420B and/or firing the cutting member 440 therethrough.

In more detail, the trigger 428 may be coupled to a pinion or gear 427 which may be operably engaged with a rack 446. Teeth of the gear 427 may suitably mesh with teeth of the rack 446 such that when a user rotates the trigger 428 towards or away from the thumb rest 432, the gear 426 rotates, thereby causing the rack 446 to translate in a distal or proximal direction, as indicated by the arrows demarcated "D" and "P," respectively. The rack 446 may be coupled to the cutting member 440. Accordingly, movement of the trigger relative to the thumb rest 432 may cause the gear 427 to rotate, which may cause the rack 446 to translate, which may subsequently cause the cutting member 440 and/or the closure beam 470 to also translate with respect to the jaws 420A, 420B as described above in various embodiments.

The gear 427 and/or rack 446 may further comprise one or more enlarged or otherwise abnormal teeth that may cause the user to feel an interference, hear a click, and/or receive any other suitable haptic feedback during the rotation of the trigger 428 relative to the thumb rest 432, for example. Such haptic feedback may be provided when the trigger 428 is at a certain predefined position or positions, such as positions 491, 492, and/or 493. The first position 491 may correlate with the end effector 410 in an initial, open position as shown. Pulling the trigger 428 to the second position 492 may provide haptic feedback correlating with the jaws 420A, 420B being in a closed position. The third position 493 may correlate with the cutting member 440 being at the fully advanced position (not shown; see the relative position of cutting member 240 in FIG. 18, for example). Accordingly, a user may be provided with haptic feedback when the end effector 410 is at a various stages, which may be helpful when the user cannot see the end effector 410, for instance, when the surgical instrument 400 is being used during a surgical procedure and the end effector 410 is inside a patient's body.

In at least one embodiment, the surgical instrument 400 may be electrically coupled to a controller 150 and an electrical source 145 via a cable 152 as described above. In such embodiments, the end effector 410 may comprise energy delivery surfaces 475A, 475B, similar to energy delivery surfaces 175A, 175B also described above. The energy delivery surfaces 475A, 475B may be electrically coupled with the cable 152 such that electrical energy may be provided to the surfaces 475A and/or 475B. In such embodiments, the trigger 428 may cause the controller 150 to allow the electrical source to provide electrical current to the energy delivery surfaces 475A and/or 475B when the trigger is at a certain predetermined position or positions. For example, the trigger 428 may be electrically coupled to the controller 145 such that as the trigger is moved to an intermediate position, sequentially between the second position 492 and the third position 493, the energy delivery surfaces 475A and/or 475B may be energized when the trigger is at the intermediate position. Accordingly, a user may squeeze the trigger 428 to the second position 492, again correlating with the jaws 420A, 420B in a closed configuration, and then the user may know that shortly after continuing to squeeze the trigger 428 toward the third position 493, the energy delivery surfaces 475A and/or 475B may be activated to weld tissue. The intermediate position correlating with the energy activation, may be configured such that electrical current begins to flow to the energy delivery surfaces 475A and/or 475B before the cutting member 440 begins to enter the space or gap between the jaws 420A, 420B. Such a configuration may allow outer tissue layers, such as a vessel's outer adventitia layers, for example, to be compressed before energy is applied thereto. Accordingly, target tissue may be welded, ablated, sealed, or otherwise energetically modified before the cutting member begins to sever the target tissue.

Figure 30:
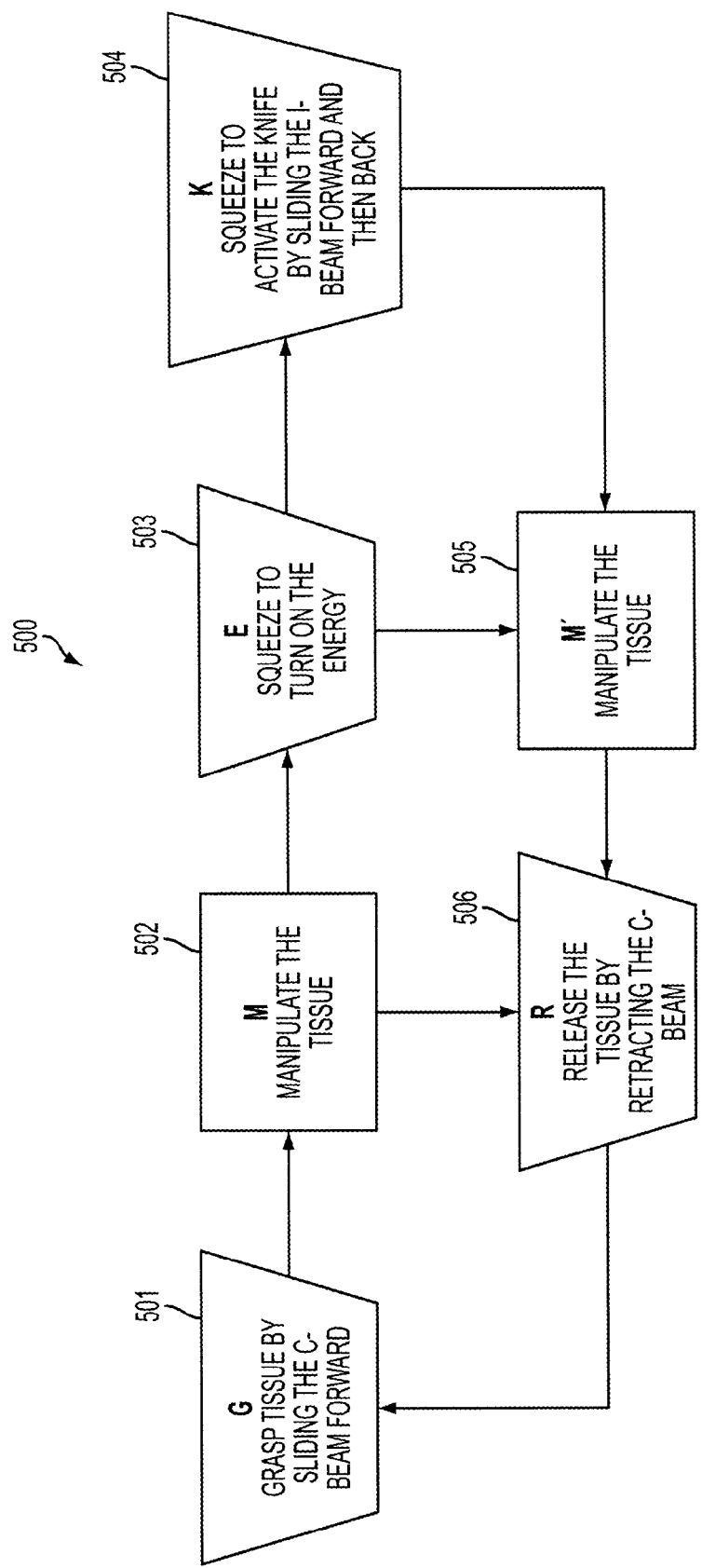
FIG. 30 is a flowchart showing various stages or states of operation of a surgical instrument according to a non-limiting embodiment.

FIG. 30 illustrates a flowchart 500 showing the various stages or states of a surgical instrument according to one or more embodiments herein. State "G" 501 is reached when tissue is grasped by sliding a closure beam, such as closure beams 170, 270, 370, and/or 470, for example, forward, towards, and/or into a jaw, such as jaw 120A, 220A, 320A, and/or 420A, for example, such that the jaw closes. From state G 501, the tissue may be manipulated. The tissue may be released by retracting the closure beam to reach state "R" 506, after which states G and M, 501 and 502, respectively, may be revisited. After sufficiently manipulating the tissue at state M 502, the user may activate the energy delivery surfaces, such as energy delivery surfaces 175A, 175B, 475A, and/or 475B, for example, by continuing to squeeze a trigger, such as trigger 128 and/or 428, for example, to create a first sealed tissue area. The tissue may be manipulated further at state "M'" 505 by keeping the jaws closed. Thereafter, the tissue may be released at state R 506 and then re-grasped at a different position, for example, one that is contiguous with the first sealed tissue area, at state G 501 again. The tissue may again be manipulated at state M 502 and then sealed at state E 503 again to create a second sealed area. This may be repeated until a sufficient sealed area is created. Thereafter, the sealed tissue may be cut or severed at state "K" 504 by squeezing the trigger further such that a cutting member, such as cutting member 140, 240, 340, and/or 440, for example, slides distally and then proximally after cutting the tissue. Then, the cut and sealed tissue may be manipulated again at state M' 505 and finally released at state R 506. The process may then be repeated to grasp (state G 501), manipulate (state M 502), energetically seal (state E 503), cut (state K 504), re-manipulate (state M' 505), and/or release (state R 506) another targeted tissue area.

The embodiments of the devices described herein may be introduced inside a patient using minimally invasive or open surgical techniques. In some instances it may be advantageous to introduce the devices inside the patient using a combination of minimally invasive and open surgical techniques. Minimally invasive techniques may provide more accurate and effective access to the treatment region for diagnostic and treatment procedures. To reach internal treatment regions within the patient, the devices described herein may be inserted laparoscopically, such as in a multiple site laparoscopy, a single site laparoscopy, or a single incision laparoscopic surgery, for example. Further, the devices described here may be used in a single port access procedure, for example. Additionally or alternatively, the devices described herein may be inserted through natural openings of the body such as the mouth, anus, and/or vagina, for example. Minimally invasive procedures performed by the introduction of various medical devices into the patient through a natural opening of the patient are known in the art as NOTES™ procedures. Some portions of the devices may be introduced to the tissue treatment region percutaneously or through small—keyhole—incisions.

Endoscopic minimally invasive surgical and diagnostic medical procedures are used to evaluate and treat internal organs by inserting a small tube into the body. The endoscope may have a rigid or a flexible tube. A flexible endoscope may be introduced either through a natural body opening (e.g., mouth, anus, and/or vagina) or via a trocar through a relatively small—keyhole—incision (usually 0.5-1.5 cm). The endoscope can be used to observe surface conditions of internal organs, including abnormal or diseased tissue such as lesions and other surface conditions and capture images for visual inspection and photography. The endoscope may be adapted and configured with working channels for introducing medical instruments to the treatment region for taking biopsies, retrieving foreign objects, and/or performing surgical procedures.

The devices disclosed herein may be designed to be disposed of after a single use, or they may be designed to be used multiple times. In either case, however, the device may be reconditioned for reuse after at least, one use. Reconditioning may include a combination of the steps of disassembly of the device, followed by cleaning or replacement of particular pieces, and subsequent reassembly. In particular, the device may be disassembled, and any number of particular pieces or parts of the device may be selectively replaced or removed in any combination. Upon cleaning and/or replacement of particular parts, the device may be reassembled for subsequent use either at a reconditioning facility, or by a surgical team immediately prior to a surgical procedure. Those of ordinary skill in the art will appreciate that the reconditioning of a device may utilize a variety of different techniques for disassembly, cleaning/replacement, and reassembly. Use of such techniques, and the resulting reconditioned device, are all within the scope of this application.

Preferably, the various embodiments of the devices described herein will be processed before surgery. First, a new or used instrument is obtained and if necessary cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility. Other sterilization techniques can be done by any number of ways known to those skilled in the art including beta or gamma radiation, ethylene oxide, and/or steam.

Although the various embodiments of the devices have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:
1. A surgical instrument, comprising:
an end effector comprising:
a first jaw defining a channel;
a second jaw, wherein the first jaw and the second jaw are operably coupled together such that the first jaw may move between an open position and a closed position with respect to the second jaw;
a closure beam sized and configured to fit at least partially within the channel, wherein the closure beam is configured to translate along the channel between a first position and a second position, wherein the first jaw is at the closed position when the closure beam is at the second position; and
a cutting member sized and configured to fit at least partially within the channel, wherein the cutting member is configured to translate along the channel and with respect to the closure beam.
2. The surgical instrument of claim 1, further comprising an interlocking member configured to selectively hold the cutting member and the closure beam together such that the cutting member and the closure beam translate synchronously with each other in at least one direction with respect to the first jaw.

3. The surgical instrument of claim 2, wherein the interlocking member comprises a pawl rotatably mounted to one of the closure beam and the cutting member.

4. The surgical instrument of claim 2, wherein the interlocking member comprises a nub protruding from the cutting member, wherein the nub is configured to engage the closure beam, and wherein the second jaw further comprises a ramped surface that is configured to move the cutting member away from the closure beam and disengage the nub from the closure beam.

5. The surgical instrument of claim 1, wherein the cutting member is sized and configured to at least partially fit within the closure beam.

6. The surgical instrument of claim 1, wherein the cutting member defines a longitudinal axis, wherein the cutting member protrudes from the closure beam in a direction transverse to the longitudinal axis.

7. The surgical instrument of claim 1, further comprising a handle operably coupled to the end effector, wherein the handle comprises a body and a trigger extending from the body, wherein the trigger is configured to move with respect to the body, and wherein the trigger is operably coupled to the cutting member such that the cutting member translates with respect to the first jaw when the trigger moves with respect to the body.

8. The surgical instrument of claim 7, wherein the trigger is configured to actuate the closure beam and the cutting member such that the closure beam and the cutting member translate with respect to the first jaw.

9. The surgical instrument of claim 7, wherein the handle trigger is configured to provide haptic feedback at predetermined positions of the trigger relative to the handle body.

10. The surgical instrument of claim 1, wherein the first jaw comprises an inner camming surface, and wherein the closure beam is positioned to engage the inner camming surface.

11. The surgical instrument of claim 1, wherein the first jaw comprises a distal end, and wherein the second position is aligned with the distal end.

12. The surgical instrument of claim 1, wherein the first position and the second position define a longitudinal axis, and wherein the cutting member is configured to translate along the longitudinal axis to a distal portion of the first jaw.

13. The surgical instrument of claim 1, wherein a slot is defined in the closure beam, and wherein the cutting member comprises an upper flange moveably positioned in the slot.

14. The surgical instrument of claim 1, wherein the cutting member comprises a lower flange comprising a lower camming surface.

15. The surgical instrument of claim 1, wherein the first jaw comprises a body and at least one electrode embedded in the body.

16. The surgical instrument of claim 1, wherein the channel longitudinally bisects the first jaw.

17. A surgical instrument, comprising:
an end effector comprising:
a first jaw comprising a tissue contacting surface;
a second jaw, wherein the first jaw and the second jaw are operably coupled together such that the first jaw may move between an open position and a closed position with respect to the second jaw;
a closure beam operably contacting the first jaw, wherein the closure beam is configured to translate with respect to the first jaw between a first position and a second position, and wherein the first jaw is urged into the closed position by the closure beam when the closure beam is at the second position;
a cutting member defining a longitudinal axis, wherein the cutting member is configured to translate with respect to the first jaw between a retracted position and a fully advanced position, and wherein the cutting member is configured to translate with respect to the closure beam; and
an interlocking member configured to selectively hold the cutting member and the closure beam together such that the cutting member and the closure beam translate synchronously with each other in at least one direction with respect to the first jaw.

18. The surgical instrument of claim 17, wherein the interlocking member comprises a pawl rotatably mounted to one of the closure beam and the cutting member.

19. The surgical instrument of claim 17, wherein the interlocking member comprises a nub protruding from the cutting member, wherein the nub is configured to engage the closure beam, and wherein the second jaw further comprises a ramped surface contacting at least a portion of the cutting member.

20. A surgical instrument, comprising:
an end effector comprising:
a first jaw;
a second jaw, wherein the first jaw and the second jaw are operably coupled together such that the first jaw may move between an open position and a closed position with respect to the second jaw;
a closure beam, wherein the closure beam is configured to translate with respect to the first jaw between a first position and a second position, wherein the first jaw is urged into the closed position by the closure beam when the closure beam is at the second position;
a cutting member configured to translate with respect to the first jaw, wherein the cutting member is configured to translate with respect to the closure beam; and
an interlocking member configured to selectively hold the cutting member and the closure beam together such that the cutting member and the closure beam translate synchronously with each other in at least one direction with respect to the first jaw.

21. The surgical instrument of claim 20, further comprising a handle operably coupled to the end effector, wherein the handle comprises a body and a trigger extending from the body, wherein the trigger is configured to move with respect to the body, wherein the trigger is operably coupled to the cutting member such that the cutting member translates with respect to the first jaw when the trigger moves with respect to the body.

22. The surgical instrument of claim 21, wherein the cutting member is configured to translate with respect to the first jaw between a retracted position and a fully advanced position, wherein the trigger is configured to move sequentially between a first position, a second position, and a third position;
wherein the first jaw is at the open position when the trigger is at the first position;
wherein the first jaw is at the closed position when the trigger is at the second position;
wherein the cutting member is at the fully advanced position when the trigger is at the third position.

23. The surgical instrument of claim 22, wherein the end effector further comprises at least one energy delivery surface, wherein the trigger is configured to move to an intermediate position sequentially between the second and third positions, wherein the energy delivery surface is energized when the trigger is at the intermediate position.

24. The surgical instrument of claim 20, wherein the interlocking member comprises a pawl rotatably mounted to the closure beam or to the cutting member.

25. The surgical instrument of claim 20, wherein the interlocking member comprises a nub protruding from the cutting member, wherein the nub is configured to engage the closure beam, and wherein the second jaw further comprises a ramped surface contacting at least a portion of the cutting member.

26. The surgical instrument of claim 25, wherein the closure beam comprises a detent that is configured to releasably receive the nub.

* * * * *